(12) United States Patent
Mailman et al.

(10) Patent No.: US 6,916,823 B2
(45) Date of Patent: Jul. 12, 2005

(54) METHOD OF TREATMENT OF DOPAMINE-RELATED DYSFUNCTION

(75) Inventors: Richard B. Mailman, Chapel Hill, NC (US); David E. Nichols, West Lafayette, IN (US); Xuemei Huang, Chapel Hill, NC (US)

(73) Assignees: Purdue Research Foundation, West Lafayette, IN (US); University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/050,289

(22) Filed: Jan. 16, 2002

(65) Prior Publication Data

US 2002/0132827 A1 Sep. 19, 2002

Related U.S. Application Data

(60) Provisional application No. 60/261,889, filed on Jan. 16, 2001.

(51) Int. Cl.$^7$ ............................................. A61K 31/44
(52) U.S. Cl. ...................................... 514/284; 514/285
(58) Field of Search ................................ 514/284, 285, 514/229.5

(56) References Cited

U.S. PATENT DOCUMENTS 6,194,423 B1 * 2/2001 Nichols et al. ............. 514/280

OTHER PUBLICATIONS

"Dinapsoline: Characterization of a D1 Dopamine Receptor Agonist in a Rat Model of Parkinson's Disease," Gulwadi, et al. *J. Pharm. and Exper. Ther.* 296: 338–344 (2001).
"Dyskinesias and Tolerance Induced by Chronic Treatment with a D1 Agonist Administered in Pulsatile or Continuous Mode Do Not Correlate with Changes of Putaminal D1 Recptors in Drug–Naive MPTP Monkeys," Goulet, et al. *Brain Res.* 719: 129–137 (1996).
"Potential Therapeutic Use of the Selective Dopamine D1 Receptor Agonist, A–86929: An Acute Study in Parkinsonian Levodopa–Primed Monkeys," Grondin et al. *Neurology* 49: 421–426 (1997).
"Time Interval Between Repeated Injections Conditions the Duration of Motor Improvement to Apomorphine in Parkinson's Disease," Grandas et al. *Neurology* 42: 1287–1290 (1992).
"Increased or Decreased Locomotor Response in Rats Following Repeated Administration of Apomorphine Depends on Dosage Interval," Castro et al. *Psychopharm.* 85: 333–339 (1985).
"Time Course of Tolerance to Apomorphine in Parkinsonism," Gancher et al. *Clin. Pharmacol. Ther.* 52: 504–510 (1992).
"Characterization of the D1 Agonist Dinapsoline in the Unilateral 6–OHDA Lesioned Rat," Taber et al. Society for Neuroscience Abstr. 26: Abstr. 809.3 (2000).
"The Selective Dopamine D1 Receptor Agonist A–86929 Maintains Efficacy with Repeated Treatment in Rodent and Primate Models of Parkinson's Disease," Asin et al. *J. Pharm. and Exper. Ther.* 281: 454–459 (1997).
"Persistent Activation of the Dopamine D1 Receptor Contributes to Prolonged Receptor Desensitization: Studies with A–77636," Lin et al. *J. Pharm. and Exper. Ther.* 276: 1022–1029 (1996).

* cited by examiner

*Primary Examiner*—Sreeni Padmanabhan
*Assistant Examiner*—Jennifer Kim
(74) *Attorney, Agent, or Firm*—Barnes & Thornburg LLP

(57) ABSTRACT

The present invention relates to the treatment of dopamine-related dysfunction using full $D_1$ dopamine receptor agonists in an intermittent dosing protocol with a short, but essential, "off-period." The $D_1$ agonist concentration is reduced during the "off-period" to obtain a plasma concentration of agonist that suboptimally activates $D_1$ dopamine receptors for a period of time to prevent induction of tolerance. Specifically, the method comprises the steps of periodically administering to a patient a full $D_1$ agonist with a half-life of up to about 6 hours at a dose resulting in a first plasma concentration of agonist capable of activating $D_1$ dopamine receptors to produce a therapeutic effect. The dose is reduced at least once every 24 hours to obtain a second lower plasma concentration of agonist that results in suboptimal activation of $D_1$ dopamine receptors for a period of time sufficient to prevent induction of tolerance.

13 Claims, 6 Drawing Sheets

METHOD OF TREATMENT OF DOPAMINE-RELATED DYSFUNCTION

CROSS REFERENCE TO RELATED APPLICATIONS

This application claims priority under 35 U.S.C. § 119(e) to U.S. Provisional Application No. 60/261,889, filed Jan. 16, 2001 expressly incorporated by reference herein.

GOVERNMENT RIGHTS

Research relating to this invention was supported in part by the U.S. Government under Grant No. MH40537 awarded from the National Institutes of Health. The U.S. Government may have certain rights in this invention.

FIELD OF THE INVENTION

The present invention relates to the treatment of disorders resulting from dopamine-related dysfunction using full $D_1$ dopamine receptor agonists. More particularly, the invention relates to using full $D_1$ dopamine receptor agonists in an intermittent dosing protocol to treat disorders resulting from dopamine-related dysfunction.

BACKGROUND AND SUMMARY OF THE INVENTION

Dopamine is a neurotransmitter in the central nervous system that has been implicated in the etiology and treatment of several neurological and psychiatric disorders, such as schizophrenia, narcolepsy, restless leg syndrome, and Parkinson's disease, and of other disorders such as shock, including septic shock, congestive heart failure, arrhythmias, hypotension, and hypertension. Exemplary of these disorders, Parkinson's disease is a neurological disorder characterized by an inability to control the voluntary motor system. Parkinson's disease involves the progressive degeneration of dopaminergic neurons, and, thus, Parkinson's disease results from insufficient dopaminergic activity. The principal approach in pharmacotherapy of Parkinson's disease has been dopamine replacement therapy using L-DOPA (L-dihydroxyphenylalanine or levodopa), a drug that can provide significant palliative effects for several years. The principal limitations of the long-term use of L-DOPA, however, include the development of unpredictable "on-off" phenomena, dyskinesias, psychiatric symptoms such as hallucinations, and eventual loss of efficacy.

To avoid these adverse events, direct-acting dopamine receptor agonists targeted for specific classes of dopamine receptors have been tried. Dopamine receptors have traditionally been classified into two families (the $D_1$ and $D_2$ dopamine receptor families) based on pharmacological and functional evidence. $D_1$ receptors generally lead to stimulation of the enzyme adenylate cyclase, whereas $D_2$ receptors often are coupled negatively (or not at all) to adenylate cyclase. Dopamine receptors are further classified by their agonist (receptor activating) or antagonist (receptor blocking) activity.

$D_2$-preferring agonists, such as bromocriptine, ropinirole, and pramipexole, have been found to be useful in the early stages of Parkinson's disease, losing efficacy as the illness progresses. Efforts to develop $D_1$ agonists for the treatment of Parkinson's disease have met with limited success. For example, SKF-38393 and CY 208–243 were efficacious in rodent models, but were less effective in parkinsonian primates or humans. These compounds are partial agonists at $D_1$ receptors suggesting the need for full intrinsic activity at the $D_1$ receptor. The differentiation between $D_1$ agonists of full and partial efficacy is important because this may influence the actions of dopamine receptor agonists on complex central nervous system mediated events.

This hypothesis is supported by recent studies showing that several $D_1$ receptor full agonists are efficacious in non-human primate Parkinson's disease models and in humans with Parkinson's disease. Accordingly, researchers have directed their efforts to design ligands that are full agonists (i.e., have full intrinsic efficacy) for the $D_1$ receptor. One such compound is dihydrexidine, a hexahydrobenzo[a]phenanthridine of the formula:

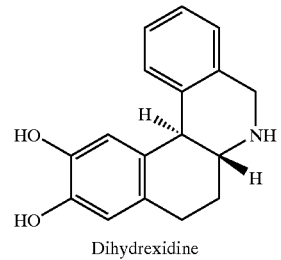

Dihydrexidine

The structure of dihydrexidine is unique from other $D_1$ agonists because the accessory ring system is tethered, making the molecule relatively rigid. The dihydrexidine-based model has served as the basis for the design of additional $D_1$ receptor agonists. The design and synthesis of $D_1$ receptor agonists having high intrinsic activity is important to the medical research community due to the potential use of full agonists to treat complex central nervous system mediated events, and also conditions in which peripheral dopamine receptors are involved.

Among the $D_1$ receptor agonists with full intrinsic activity developed based on the dihydrexidine model is a novel class of dopamine receptor agonists of the general formula:

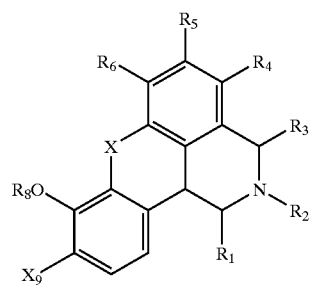

Two such compounds are dinoxyline and dinapsoline, fused isoquinolines of the formulas:

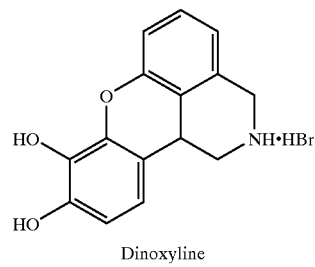

Dinoxyline

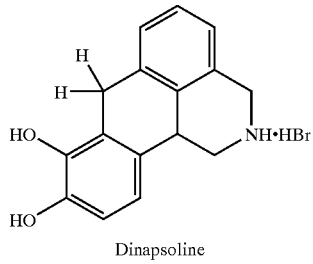

Dinapsoline

Dihydrexidine, dinoxyline, and dinapsoline function as full agonists of $D_1$ receptors. However, many full agonists have not evolved for clinical use either due to pharmacokinetic limitations or rapid development of tolerance (i.e., loss of therapeutic effects despite administration of the same or larger doses of drug). Therefore, requirements for $D_1$ agonists for Parkinson's disease therapy and for treatment of other neurological disorders and conditions involving peripheral dopamine receptors, include full intrinsic efficacy at $D_1$ receptors and failure to induce tolerance.

The present invention provides a method of treating disorders resulting from dopamine-related dysfunction, such as Parkinson's disease, by using a full $D_1$ dopamine receptor agonist in an intermittent dosing protocol. According to this protocol, the plasma concentration of the $D_1$ agonist is reduced to a concentration below the level required for optimal dopamine receptor stimulation (e.g., the concentration of the $D_1$ agonist at the D1 receptor can be decreased to a level such that receptor occupation is negligible (<5% high affinity)) for a time sufficient (i.e., at least one hour per each 24 hour period) to prevent the induction of tolerance. This dosing protocol is useful for treating patients having a dopamine-related dysfunction of the central nervous system (as evidenced by an apparent neurological, psychological, physiological, or behavioral disorder), as well as conditions in which peripheral dopamine receptors are involved (including target tissues such as the kidney, lung, endocrine, and cardiovascular systems).

In one embodiment of the invention, a method of treating a disorder resulting from dopamine-related dysfunction is provided. The method comprises the steps of administering to a patient a full $D_1$ agonist wherein said agonist has a half-life of less than 6 hours and wherein said agonist is administered at a dose resulting in a first plasma concentration of agonist capable of activating $D_1$ dopamine receptors to produce a therapeutic effect, and reducing said agonist dose at least once every 24 hours to obtain a second lower plasma concentration of agonist wherein said second concentration of agonist results in suboptimal activation of $D_1$ dopamine receptors for a period of time sufficient to prevent induction of tolerance.

In another embodiment of the invention the agonist is selected from the group consisting of dinapsoline, dinoxyline, dihydrexidine, other $D_1$ agonists, analogs and derivatives of these agonists, and combinations thereof.

In yet another embodiment of the invention, the disorder is selected from the group consisting of Parkinson's disease, autism, attention deficit disorder, schizophrenia, restless leg syndrome, memory loss, and sexual dysfunction.

BRIEF DESCRIPTION OF THE DRAWINGS

FIG. 1A shows cumulative rotation (mean±S.E.M.; n=12/group) over 10 hours for rats treated with various subcutaneous doses of dinapsoline. FIG. 1B shows the mean rotations for each 15 minute time period during a 10 hour test period in rats treated with various doses of dinapsoline.

FIG. 2A shows cumulative rotation (mean±S.E.M.; n=8/group) over 10 hours for rats treated with various oral doses of dinapsoline, and the data shown in FIG. 2B represent mean rotations (mean±S.E.M.; n=8/group) for each 15 minute time period during an 8 hour test period for rats treated with various doses of dinapsoline.

FIGS. 3A and B show cumulative rotation (mean±S.E.M.; n=8/group) over 3 hours in rats treated with various subcutaneous doses of dinapsoline and the effect on the rotational response by SCH-23390 (0.5 mg/kg s.c.) and by raclopride (2 mg/kg s.c.).

FIG. 4 shows cumulative rotation (mean±S.E.M.; n=5/group) over 3 hours after daily subcutaneous dosing once or twice per day with dinapsoline (2 mg/kg) or A-77636 over 14 days (1 mg/kg).

FIG. 5A shows cumulative rotation (mean±S.E.M.; n=8/group) over 3 hours after daily dosing with dinapsoline (2 mg/kg) with or without raclopride (2 mg/kg) over 7 days. FIG. 5B shows cumulative rotation when the $D_2$ agonist quinpirole (0.1 mg/kg) was coadministered subcutaneously in combination with A-77636 (0.3 mg/kg) or when A-77636 was administered alone.

FIG. 6A shows cumulative rotation (mean±S.E.M.; n=8/group) per 1 hour time period at various time points following implantation of osmotic minipumps administering various concentrations of dinapsoline subcutaneously. FIG. 6B shows cumulative rotation (mean±S.E.M.) after administration of various doses of dinapsoline by osmotic minipump for 14 days.

DETAILED DESCRIPTION OF THE INVENTION

Figure 1:
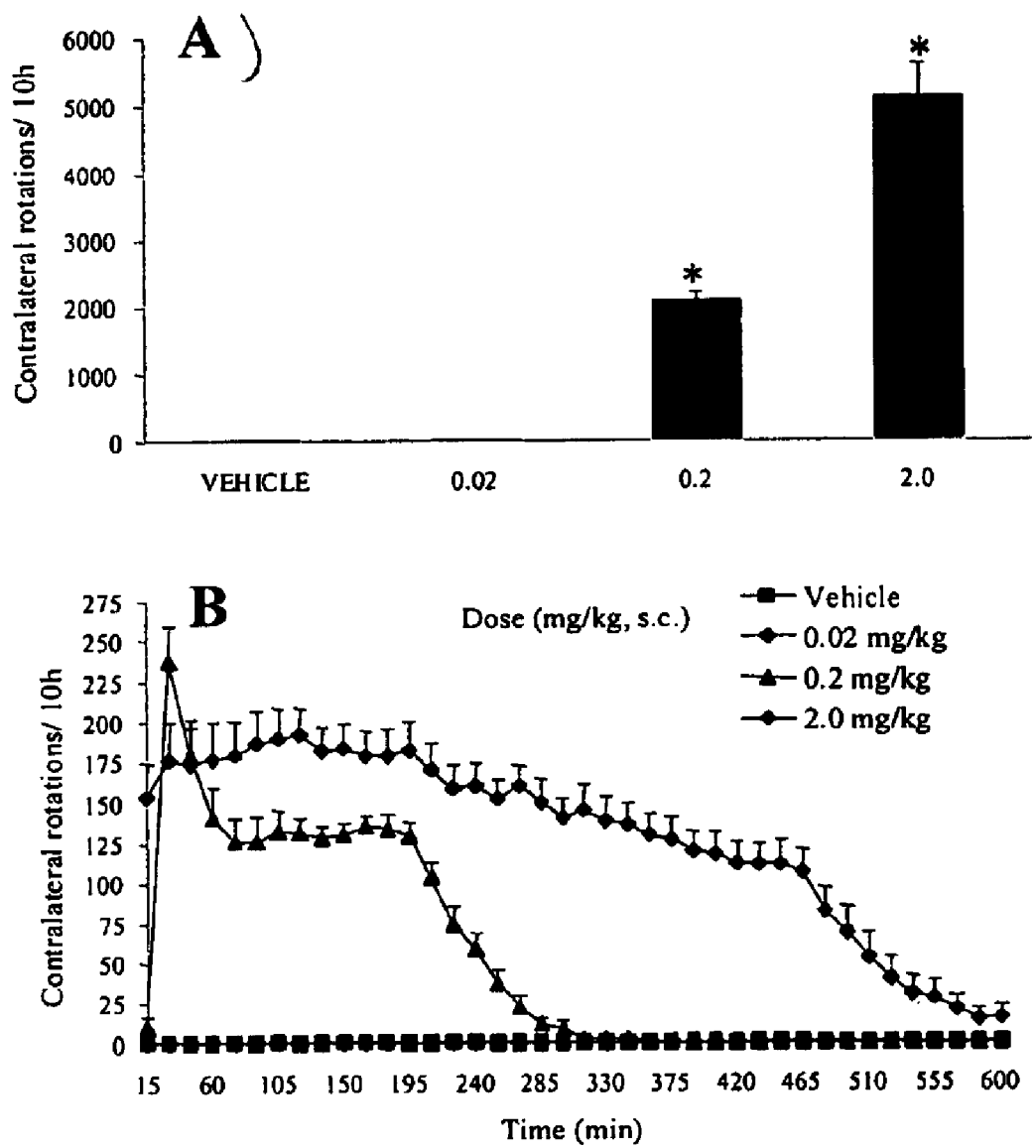
FIG. 1.

The present invention provides a method of treating disorders resulting from dopamine-related dysfunction, such as neurological and psychiatric disorders including Parkinson's disease, autism, restless leg syndrome, and schizophrenia, by using a full $D_1$ dopamine receptor agonist in an intermittent dosing protocol. According to the dosing protocol of the present invention, the full $D_1$ agonist is administered periodically to a patient at a dose resulting in a plasma concentration capable of activating $D_1$ dopamine receptors to produce a therapeutic effect. The plasma concentration of the $D_1$ agonist is then reduced to obtain a second lower tissue concentration of agonist resulting in suboptimal activation of $D_1$ dopamine receptors. The $D_1$ agonist is kept at the lower second tissue concentration for a time sufficient (i.e., at least one hour per each 24 hour period) to prevent the induction of tolerance (i.e., to prevent loss of therapeutic effect). The invention utilizes $D_1$ agonists with short pharmacokinetic half-lives (i.e., a plasma half-life of about 6 hours or less) so that the $D_1$ agonist tissue concentration can be reduced during the "off-period" to a concentration that suboptimally activates $D_1$ dopamine receptors and prevents the development of tolerance. The method embodies administration regimens that pair the pharmacokinetic characteristics of the drug being administered with the route of delivery using dosing protocols that provide the requisite receptor occupancy-time relationships. Thus, the invention provides a practical regimen that permits effective long-term therapy without the development of tolerance allowing long-term benefits to patients.

In accordance with the invention, a full $D_1$ agonist is administered periodically at a dose resulting in a plasma and receptor concentration of agonist capable of activating $D_1$ dopamine receptors. The capacity of the full $D_1$ agonist to activate $D_1$ dopamine receptors is evidenced by the presence of therapeutic effects produced by the drug. The "off-period" (i.e., at least one hour every 24 hours) comprises the subsequent reduction of the $D_1$ agonist dose to obtain a second tissue concentration of agonist that suboptimally activates $D_1$ dopamine receptors. Suboptimal activation means that the receptors either are not activated, or are not fully activated, which provides the period of decreased receptor activation that prevents the induction of tolerance. Therefore, the suboptimal activation of $D_1$ dopamine receptors is evidenced by the consequent lack of development of tolerance (i.e., the therapeutic effects of the $D_1$ agonist are retained).

It is contemplated that full $D_1$ agonists that bind irreversibly to $D_1$ dopamine receptors or bind to dopamine receptors with ultra-high affinity may not be useful in accordance with the dosing protocol of the present invention. Accordingly, full $D_1$ agonists that remain resident on $D_1$ dopamine receptors for a period of 24 hours or longer (i.e., bind irreversibly to $D_1$ dopamine receptors, or that bind to dopamine receptors with high affinity or have long residence times) may not be useful in accordance with the present invention. It is likely that these $D_1$ agonists bind so tightly to $D_1$ dopamine receptors that receptor activation would occur even when the plasma concentration of these agonists is reduced to zero.

In accordance with the dosing protocol of the present invention, the "off-period" for reduction of the administered dose of the $D_1$ dopamine agonist can be any period of time sufficient to obtain a plasma and receptor concentration of the $D_1$ agonist resulting in suboptimal activation of $D_1$ dopamine receptors preventing the induction of tolerance. The "off-period" can be produced via metered control of drug administration, for example, by administration of the $D_1$ agonist using a metering pump or by using a parenterally or orally administered sustained or pulsatile release dosage form of the drug. In one embodiment of the invention, the "off-period" is at least one hour per each 24-hour dosing period. In another embodiment of the invention, the "off-period" is about one to about four hours per each 24-hour dosing period, or any other time interval sufficient to prevent the induction of tolerance. Preferably, the "off-period" is the night sleep period. The duration of the "off-period" will depend on the receptor binding affinity of the particular $D_1$ dopamine agonist used to treat the dopamine-related dysfunction, the half-life of the $D_1$ dopamine agonist, the capacity of the $D_1$ agonist to be metabolized to an alternative active form of the drug, and other factors that may influence the capacity to decrease $D_1$ agonist binding to $D_1$ dopamine receptors during the "off-period" to a level that prevents induction of tolerance.

The intermittent dosing protocol of the present invention is useful for treating patients having a dopamine-related dysfunction of the central nervous system as evidenced by an apparent neurological, psychological, physiological, or behavioral disorder. Exemplary of dopamine-related disorders of the central nervous system that may be treated in accordance with the present invention are Parkinson's disease, autism, attention deficit disorder, restless leg syndrome, and schizophrenia. It is contemplated that the intermittent dosing protocol of the present invention will be effective in treating mid- and late-stage Parkinson's disease, for example, in patients no longer adequately responsive to levodopa therapy. The invention is also useful for treating patients having conditions in which peripheral dopamine receptors are involved including target tissues such as the kidney, lung, endocrine, and cardiovascular systems. Exemplary of such disorders include increasing renal perfusion in critical care medicine, and pulmonary disorders requiring increased perfusion and/or decreased vascular resistance.

Memory loss can also be treated with $D_1$ agonists in accordance with the intermittent dosing protocol of the present invention. It is contemplated that preferential occupation and activation of $D_1$-like receptors without the development of tolerance will cause neuromodulatory effects that will result in improvements in memory, cognition, and/or attention resulting in symptomatic improvement in individuals who have age-related loss of memory and cognition. The method of the present invention can also be used to treat memory loss not related to aging. For example, the intermittent dosing protocol in accordance with the present invention can improve memory loss in individuals with schizophrenia, attention deficit disorder, autism, and related central nervous system disorders.

The presently claimed intermittent dosing protocol also has beneficial effects for sexual dysfunction. In particular, the dosing protocol may be useful in the treatment of forms of secondary sexual dysfunction (i.e., where the etiology of dysfunction originates in the central nervous system). It is contemplated that sexual function may be improved for several hours after a subcutaneous injection of a full $D_1$ agonist. Such a protocol results in a period subsequent to the injection during which the tissue concentration of the $D_1$ agonist falls to a concentration at which $D_1$ dopamine receptors are suboptimally activated preventing the induction of tolerance.

Exemplary of the full $D_1$ agonists for use in accordance with the present invention are dihydrexidine, dinapsoline, dinoxyline, A86929, SKF-82958, analogs and derivatives of these $D_1$ agonists, and combinations thereof. For example, the $D_1$ agonists described in U.S. Pat. Nos. 5,597,832, 5,659,037, and 5,668,141, incorporated herein by reference, may be used. Alternatively, "masked" or "prodrug" precursors that are activated upon introduction into biological systems by hydrolysis or other metabolic processes to reveal the active "unmasked" $D_1$ agonist molecule may be used. Such "masked" or "prodrug" precursors may enhance chemical or biological stability of $D_1$ agonists. Dihydrexidine, dinapsoline, and dinoxyline have all been shown to be efficacious in Parkinson's disease models (e.g., the unilateral 6-OHDA-lesion rodent model).

Although the $D_1$ agonists for use in the present invention possess properties as full $D_1$ dopamine receptor agonists, for some patients, the agonist chosen should also have some $D_2$ agonist properties. Exemplary in Parkinson's disease, the degree and nature of the D2 properties should be individualized to maximize the therapeutic benefit to the patients, based on the relative amount of dyskinesias, emesis, and/or mental disturbance caused by prior use of levodopa and/or apomorphine. Thus, patients who have demonstrated large dyskinetic or emetic responses to levodopa or apomorphine should be given full $D_1$ agonists with greater $D_1:D_2$ selectively, or full $D_1$ agonists in which the $D_2$ properties have a high degree of functional selectively. Dihydrexidine, dinapsoline, and dinoxyline all exhibit some $D_2$ agonist properties. Dihydrexidine is ten-fold $D_1:D_2$ selective, dinapsoline is five-fold $D_1:D_2$ selective, and dinoxyline has equally high affinity for both types of receptors.

In one embodiment of the invention is provided a hexahydrobenzo-[a]phenanthridine compound of the general formula:

Formula I

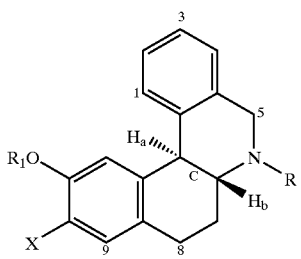

wherein $H_a$ and $H_b$ are trans across ring fusion bond c, R is hydrogen, OH, or $C_1$–$C_4$ alkyl; $R_1$ is hydrogen, benzoyl or pivaloyl; and X is hydrogen, chloro, bromo, iodo or a group of the formula —$OR_2$ wherein $R_2$ is hydrogen, benzoyl or pivaloyl. In another embodiment of this invention when X is a group of the formula —$OR_2$, the groups $R_1$ and $R_2$ can be taken together to form a —$CH_2$— group, thus representing a methylenedioxy functional group bridging the C-10 and C-11 positions on the hexahydrobenzo[a]phenanthridine ring system.

One such compound is dihydrexidine, a hexahydrobenzo[a]phenanthridine of the formula:

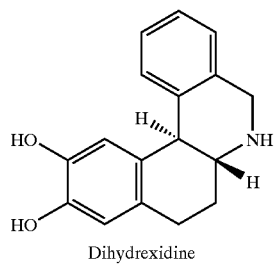

Dihydrexidine

In another embodiment of the invention is provided a substituted hexahydrobenzo[a]phenanthridine of the general formula:

Formula II

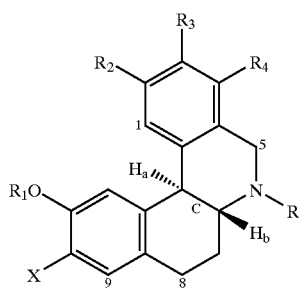

and pharmaceutically acceptable salts thereof wherein $H_a$ and $H_b$ are trans across ring fusion bond c, R is hydrogen, OH, or $C_1$–$C_4$ alkyl; $R_1$ is hydrogen or a phenoxy protecting group; and X is fluoro, chloro, bromo, iodo or a group of the formula —$OR_5$ wherein $R_5$ is hydrogen or a phenoxy protecting group, provided that when X is a group of the formula —$OR_5$ the groups $R_1$ and $R_5$ can be taken together to form a —$CH_2$— group, thus representing a methylenedioxy functional group bridging the C-10 and C-11 positions on the hexahydrobenzo[a]phenanthridine ring system; and $R_2$, $R_3$, and $R_4$ are independently selected from the group consisting of hydrogen, $C_1$–$C_4$ alkyl, phenyl, fluoro, chloro, bromo, iodo, or a group —$OR_1$ wherein $R_1$ is as defined above, provided that at least one of $R_2$, $R_3$, and $R_4$ are other than hydrogen.

In an alternate embodiment of the invention is provided a compound of the general formula:

Formula III

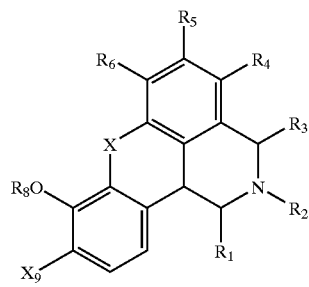

and pharmaceutically acceptable salts thereof wherein $R_1$–$R_3$ are hydrogen, $C_1$–$C_4$ alkyl or $C_2$–$C_{24}$ alkenyl; $R_8$ is hydrogen, $C_1$–$C_4$ alkyl or a phenoxy protecting group; $X_9$ is hydrogen, halo including chloro, fluoro and bromo, or a group of the formula —OR wherein R is hydrogen, $C_1$–$C_4$ alkyl or a phenoxy protecting group, X is oxygen or carbon, and $R_4$, $R_5$ and $R_6$ are independently selected from the group consisting of hydrogen, $C_1$–$C_4$ alkyl, phenyl, halo, or a group —OR wherein R is as defined above, and when $X_9$ is a group of the formula —OR, the groups $R_8$ and R can be taken together to form a group of the formula —$CH_2$—. In one embodiment at least one of $R_4$, $R_5$ or $R_6$ is hydrogen. In another embodiment at least two of $R_4$, $R_5$ or $R_6$ are hydrogen.

Two such compounds are dinoxyline and dinapsoline, fused isoquinolines of the formulas:

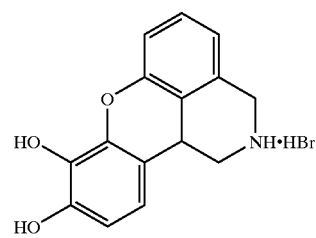

Dinoxyline

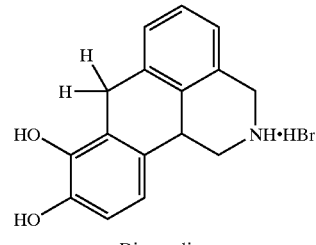

Dinapsoline

The term "$C_2$–$C_{24}$ alkenyl" with reference to all of the compounds described above refers to allyl, 2-butenyl, 3-butenyl, and vinyl.

The term "$C_1$–$C_4$ alkyl" as used herein refers to branched or straight chain alkyl groups comprising one to four carbon atoms, including, but not limited to, methyl, ethyl, propyl, isopropyl, n-butyl, t-butyl and cyclopropylmethyl.

The term "pharmaceutically acceptable salts" as used herein refers to those salts formed using organic or inorganic acids which salts are suitable for use in humans and lower animals without undesirable toxicity, irritation, allergic response and the like. Acids suitable for forming pharmaceutically acceptable salts of biologically active compounds having amine functionability are well known in the art. The salts can be prepared according to conventional methods in situ during the final isolation and purification of the present compounds, or separately by reacting the isolated compounds in free base form with a suitable salt forming acid.

The term "phenoxy protecting group" as used herein refers to substituents on the phenolic oxygen which prevent undesired reactions and degradations during synthesis and which can be removed later without effect on other functional groups on the molecule. Such protecting groups and the methods for their application and removal are well known in the art. They include ethers, such as cyclopropylmethyl, cyclohexyl, allyl ethers and the like; alkoxyalkyl ethers such as methoxymethyl or methoxyethoxymethyl ethers and the like; alkylthioalkyl ethers such as methylthiomethyl ethers; tetrahydropyranyl ethers; arylalkyl ethers such as benzyl, o-nitrobenzyl, p-methoxybenzyl, 9-anthrylmethyl, 4-picolyl ethers and the like; trialkylsilyl ethers such as trimethylsilyl, triethylsilyl, t-butyldimethylsilyl, t-butyldiphenylsilyl ethers and the like; alkyl and aryl esters such as acetates, propionates, butyrates, isobutyrates, trimethylacetates, benzoates and the like; carbonates such as methyl, ethyl, 2,2,2-trichloroethyl, 2-trimethylsilylethyl, benzyl and the like; and carbamates such as methyl, isobutyl, phenyl, benzyl, dimethyl and the like.

The term "$C_1$–$C_4$ alkoxy" as used herein refers to branched or straight chain alkyl groups comprising one to four carbon atoms bonded through an oxygen atom, including but not limited to, methoxy, ethoxy, propoxy and t-butoxy.

One compound for use in the dosing protocol of the present invention is (±)-8,9-dihydroxy-1,2,3,11b-tetrahydrochromeno[4,3,2-de]isoquinoline hydrobromide denominated as "dinoxyline." Dinoxyline is synthesized from 2,3-dimethoxyphenol, as depicted in Scheme 1. The phenolic group is protected as the methoxymethyl ("MOM") derivative followed by treatment with butyllithium, then with the substituted borolane illustrated, to afford the borolane derivative 2.

As shown in Scheme 1, this borolane derivative is then employed in a Pd-catalyzed Suzuki type cross coupling reaction with 5-nitro-4-bromoisoquinoline. The resulting coupling product 4a is then treated with toluenesulfonic acid in methanol to remove the MOM protecting group of the phenol. Simple treatment of this nitrophenol 5a with potassium carbonate in DMF at 80° C. leads to ring closure with loss of the nitro group, affording the basic tetracyclic chromenoisoquinoline nucleus 6a. Simple catalytic hydrogenation causes reduction of the nitrogen-containing ring to yield 7a. Use of boron tribromide to cleave the methyl ether linkages gives the parent compound 8a.

It is apparent that by appropriate substitution on the isoquinoline ring a wide variety of substituted compounds can be obtained. Substitution onto the nitrogen atom in either 6a or 7a, followed by reduction will readily afford a series of compounds substituted with lower alkyl groups on the nitrogen atom. Likewise, the use of alkyl substituents on the 1, 3, 6, 7, or 8 positions of the nitroisoquinoline 3a would lead to a variety of ring-substituted compounds. In addition, the 3-position of 6a can also be directly substituted with a variety of alkyl groups. Similarly, replacement of the 4-methoxy group of 2a, in Scheme 1, with fluoro, chloro, or alkyl groups leads to the subject compounds with variations at $X_9$. When groups are present on the nucleus that are not stable to the catalytic hydrogenation conditions used to convert 6a to 7a, we have found that reduction can be accomplished using sodium cyanoborohydride at slightly acidic pH. Further, formation of the N-alkyl quaternary salts of derivatives of 6a gives compounds that are also easily reduced with sodium borohydride, leading to derivatives of 7a. The synthesis of hexahydrobenzo[a]phenanthridine compounds (e.g., dihydrexidine) and substituted hexahydrobenzo[a]phenanthridine compounds is described in U.S. Pat. Nos. 5,047,536 and 5,420,134, respectively, incorporated herein by reference. The synthesis of dinapsoline is described in U.S. Pat. No. 5,959,110 also incorporated herein by reference.

Space-filling representations of the low energy conformations for (+)-trans-10,11-dihydroxy-5,6,6a,7,8,12b-hexahydrobenzo[a]phenanthridine [(+)-dihydrexidine] and the 11bR enantiomer of dinoxyline that is homochiral to (+)-dihydrexidine at its 12bS chiral center have been compared. Two major structural features are readily evident. First, the steric bulk provided by the C(7)–C(8) ethano bridge in dihydrexidine has been removed. Second, the angle of the pendent phenyl ring with respect to the plane of the catechol ring is changed slightly. This is most evident, in face-on views, where the aromatic hydrogen H(1) in dihydrexidine projects above the catechol ring. In dinoxyline, however, this position is used to tether the pendent phenyl ring through an oxygen atom, to the catechol ring; this forces the pendent phenyl ring to twist in a clockwise direction, relative to dihydrexidine, when viewed from above. The amino groups are in similar positions, given the degree of conformational flexibility of the heterocyclic rings. In addition, both molecules can present an N—H vector in an equatorial orientation, a feature of the pharmacophore believed to be important for $D_1$ receptor agonists. Consistent with those observations the pharmacological properties of these two molecules are similar.

Scheme 1

Scheme for the synthesis of 8, 9-dihydroxy-1,2,3,11b-tetrahydrochromeno[4,3,2-de]isoquinoline hydrobromide

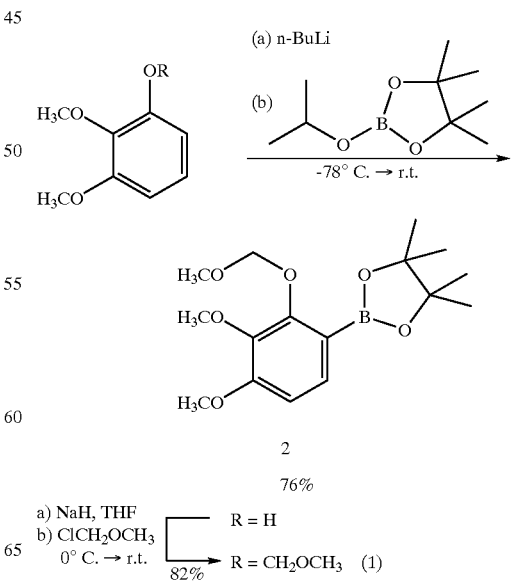

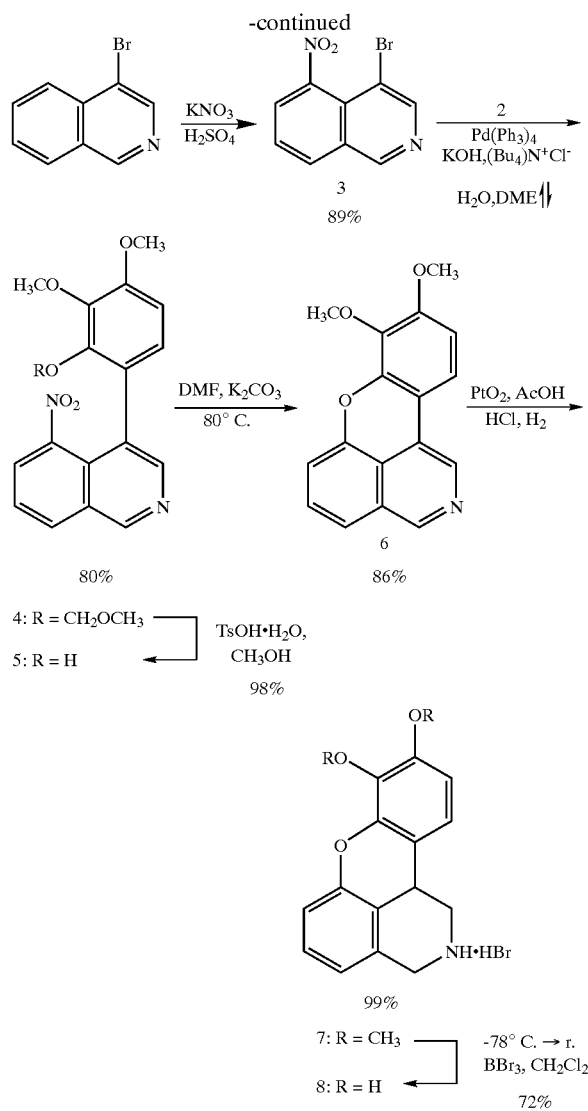

Experiments have been conducted to determine the binding affinity of dinoxyline to $D_1$ receptors. Dinoxyline was found to have similar affinity ($K_{0.5}$<5 nM) to dinapsoline for rat striatal $D_1$ receptors. In addition, competition experiments utilizing unlabeled SCH23390 as a competitor demonstrated that dinoxyline competes with SCH23390 for binding, having a shallow competition curve ($n_H$=ca. 0.7) consistent with high affinity binding agonist properties. The agonist properties of dinoxyline at $D_1$ receptors were confirmed in vitro by measuring the ability of dinoxyline to increase cAMP production in rat striatum and C-6-m$D_1$ cells. In both rat striatum and C-6-m$D_1$ cells, dinoxyline has full agonist activity with an $EC_{50}$ of less than 30 nM in stimulating synthesis of cAMP via $D_1$ receptors.

Thus, the pharmacological data confirm that dinoxyline has high affinity for dopamine $D_1$ receptors labeled with [$^3$H]SCH23390 that is slightly greater than that of (+)-trans-10,11-dihydroxy-5,6,6a,7,8,12b-hexahydrobenzo[a]phenanthridine (dihydrexidine). Moreover, dinoxyline, in both rat striatal membranes and in cloned expressed primate $D_{1A}$ receptors, was a full agonist relative to dopamine, similar to dihydrexidine but unlike the partial agonist (+)-SKF-38393.

Based on the underlying model of the $D_1$ pharmacophore, it is anticipated that both the affinity and intrinsic activity of racemic dinoxyline (and substituted analogs thereof) reside in only one of its enantiomers—the 11bR absolute configuration (and its homochiral analogs). Resolution of the racemate using art recognized separation techniques is expected to yield one dinoxyline isomer with approximately twice the $D_1$ affinity exhibited by the racemate.

In accordance with this invention the above-described compounds can be formulated in conventional drug dosage forms for treating a patient suffering from dopamine-related dysfunction of the central or peripheral nervous system. Effective doses of the above-described compounds depend on many factors, including the indication being treated, the route of administration, and the overall condition of the patient. Effective doses are those that produce a "therapeutic effect" which is a response to treatment with the full $D_1$ dopamine agonist in which one or more of the clinical symptoms of the dopamine-related dysfunction being treated in a patient are prevented, reduced, or stabilized whether such improved patient condition is permanent or temporary. In one embodiment of the invention wherein the $D_1$ agonist is administered orally, effective doses of the present compounds range from about 0.1 to about 50 mg/kg of body weight, more typically from about 0.5 to about 25 mg/kg of body weight. Effective parenteral doses can range from about 0.01 to about 15 mg/kg of body weight, more typically from about 0.1 to 5 mg/kg of body weight. In general, treatment regimens utilizing compounds in accordance with the present invention comprise administration of from about 1 mg to about 500 mg of the compounds of this invention per day in multiple doses or in a single dose.

In another embodiment of the invention wherein the $D_1$ agonist is administered orally, effective doses of the present compounds range from about 0.005 to about 10 mg/kg of body weight, more typically from about 0.005 to about 2 mg/kg of body weight. Effective parenteral doses can range from about 0.005 to about 15 mg/kg of body weight, more typically from about 0.005 to 5 mg/kg of body weight. In general, treatment regimens utilizing compounds in accordance with the present invention comprise administration of from about 0.05 mg to about 500 mg of the compounds of this invention per day in multiple doses or in a single dose.

The daily doses of full $D_1$ agonists for administration in accordance with the dosing protocol of this invention are administered periodically. "Periodically" means that the doses of agonists can be administered in single doses on a daily basis or in a multiple-dose daily regimen. Thus, in one embodiment of the invention the doses of $D_1$ agonists can be administered periodically, for example, 1 to 10 times a day. In another embodiment of the invention the doses of $D_1$ agonists can be administered, for example, 1 to 5 times a day. In another embodiment of the invention, the doses of agonist are administered once each day on a daily regimen. Any other single dose or multiple-dose daily regimen comprising periodic administration of the $D_1$ agonist that produces a therapeutic effect may be used. Further, an "off-period" is required which is at least one hour per every 24-hour dosing period, and, preferably the "off-period" is the night sleep period.

Liquid dosage forms for oral administration of $D_1$ agonists include pharmaceutically acceptable emulsions, microemulsions, solutions, suspensions, and syrups containing inert diluents commonly used in the art, such as water or oil. Such compositions may also comprise adjuvants such as wetting agents, emulsifying and suspending agents, sweetening, and flavoring agents. Liquid dosage forms may also include sprays formulated for intranasal administration using matrices and formulations that control the absorption and duration of the administered drug. Using this dosage form, the "off-period" can be set to occur, for example, during the night sleep period.

The compounds of this invention can also be formulated as solid dosage forms for oral administration such as capsules, tablets, powders, pills, lozenges and the like. Typically the active compound is admixed with an inert diluent or carrier such as sugar or starch and other excipients appropriate for the dosage form. Thus, tableting formulations will include acceptable lubricants, binders and/or disintegrants. Optionally powder compositions comprising an active compound of this invention and, for example, a starch or sugar carrier can be filled into gelatin capsules for oral administration. Other oral dosage forms of the compounds of the present invention can be formulated using art-recognized techniques in forms adapted for the specific mode of administration.

Parenteral administration can be accomplished by injection of a liquid dosage form of the $D_1$ agonist, such as by injection of a solution of the compound dissolved in a pharmaceutically acceptable buffer. The parenteral formulations can be sterilized using art-recognized microfiltration techniques. Such parenteral administration may be intradermal, subcutaneous, intramuscular, intrathecal, intraperitoneal, or intravenous. In one embodiment of the invention, the $D_1$ agonist is administered parenterally using a metering pump that controls both the dose and rate of administration of the drug. In such an embodiment of the invention, drug administration can be performed using an external metering pump that is changed, for example, daily or weekly. Alternatively, an implanted metering pump that is refilled as required, and changed over longer periods (for example, biweekly or monthly) can be used. For some patients, the daily drug infusion rates using a metering pump may be varied in a sinusoidal fashion during the drug administration period. For example, in most cases where such metering is performed, the sine period will be inversely proportional to the pharmacokinetic half-life of the full $D_1$ agonist administered.

In accordance with one embodiment of the present invention a pharmaceutical composition is injected comprising therapeutically effective amounts of a $D_1$ agonist or combinations of $D_1$ agonists, and a pharmaceutically acceptable carrier therefor. "Therapeutically effective amounts" of $D_1$ agonists are amounts of the compounds which prevent, reduce, or stabilize one or more of the clinical symptoms of a dopamine-related dysfunction whether such improved patient condition is permanent or temporary. In pharmaceutical compositions containing more than one $D_1$ agonist, the $D_1$ agonists may be present in the pharmaceutical composition at different weight ratios.

Parenteral dosage forms of the compounds of the present invention can be formulated utilizing art-recognized products by dispersing or dissolving an effective dose of the compound in a pharmaceutically acceptable carrier such as water, or more preferably, an isotonic sodium chloride solution. A "pharmaceutically acceptable carrier" for use in accordance with the invention is compatible with other reagents in the pharmaceutical composition and is not deleterious to the patient. Thus, the $D_1$ agonists for use in accordance with the dosing protocol of the present invention can be adapted for parenteral administration in accordance with this invention using a pharmaceutically acceptable carrier adapted for use in a liquid dose form. The $D_1$ agonist can be administered dissolved in a buffered aqueous solution in the form of a clarified solution or a suspension. Exemplary of a buffered solution suitable as a carrier of $D_1$ agonists administered parenterally in accordance with this invention is phosphate buffered saline prepared as follows:

A concentrated (20×) solution of phosphate buffered saline (PBS) is prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The solution is sterilized by autoclaving at 15 pounds of pressure for 15 minutes and is then diluted with additional water to a single strength concentration prior to use.

The $D_1$ agonists for use in the dosing protocol of the present invention can also be administered using sustained or pulsatile release dosage forms of the drugs. Such drug delivery systems are engineered to deliver therapeutic agents with a sustained or pulsatile release profile, and can be used to control both the dose and rate of administration of the drug. For example, sustained or pulsatile release dosage forms comprising a hydrogel composition can used and can be administered to a patient in an unencapsulated form, for example, suspended or dispersed in a liquid or solid carrier, or in an encapsulated form, such as a capsule for oral administration or microspheres for parenteral administration.

Furthermore, single- or multi-layered microspheres can be used for chronopharmacological drug delivery providing a versatile drug delivery system that can be used for delivering single therapeutic agents in single doses or multiple sequential doses, or to deliver multiple therapeutic agents in sequential doses. These delivery systems are also capable of being used to deliver therapeutic agents in versatile release patterns, including recurring doses or prolonged release doses, or combinations thereof. Additionally, drug-free intervals can be interspersed with pulsed doses or prolonged release doses to provide the "off-period" in accordance with the dosing protocol of the present invention.

Antioxidants may be administered to the patient in combination with the $D_1$ agonists in the intermittent dosing protocol of the present invention to prevent, for example, quinone formation or the introduction of additional double bonds into the $D_1$ agonists described above. Exemplary of antioxidants that may be used are naturally-occurring antioxidants, such as beta-carotene, vitamin E, vitamin C, and tocopherol, or synthetic antioxidants, such as butylated hydroxytoluene, butylated hydroxyanisole, tertiary-butylhydroquinone, propyl gallate or ethoxyquin. Compounds that act synergistically with antioxidants can also be added such as ascorbic acid (i.e., D-ascorbate), citric acid, and phosphoric acid. The amount of antioxidants incorporated in this manner depends on requirements such as packaging methods and desired shelf-life of pharmaceutical compositions.

It is known that dopamine receptor agonists may induce emesis, and, thus, antiemetic agents are often administered to patients in combination with dopamine receptor agonists. Antiemetic agents that may be used in combination with $D_1$ agonists in the dosing protocol of the present invention include $D_2$ antagonists, 5-$HT_3$ antagonists, corticosteroids, cannabinoids, antihistamines, muscarinic antagonists, and benzodiazepines or combinations thereof. These agents are available for oral administration, parenteral administration, and for administration as suppositories.

EXAMPLE 1

Synthesis of 8,9-Dihydroxy-1,2,3,11b-tetrahydrochromeno [4,3,2-de]isoquinoline Hydrobromide (Dinoxyline)

With reference to the following described experimental procedures, melting points were determined with a Thomas- Hoover melting point apparatus and are uncorrected. $^1$H NMR spectra were recorded with a Varian VXR 500S (500 MHZ) NMR instrument and chemical shifts were reported in values (ppm) relative to TMS. The IR spectra were recorded as KBr pellets or as a liquid film with a Perkin Elmer 1600 series FTIR spectrometer. Chemical ionization mass spectra (CIMS) were recorded on a Finnigan 4000 quadruple mass spectrometer. High resolution CI spectra were recorded using a Kratos MS50 spectrometer. Elemental analysis data were obtained from the microanalytical laboratory of Purdue University, West Lafayette, Ind. THF was distilled from benzophenone-sodium under nitrogen immediately before use and 1,2-Dichloroethane was distilled from phosphorous pentoxide before use.

1,2-Dimethoxy-3-methoxymethoxybenzene (1a).

A slurry of sodium hydride was prepared by adding 1000 ml of dry THF to 7.06 g (0.18 mol) of sodium hydride (60% dispersion in mineral oil) under an argon atmosphere at 0° C. To the slurry, 2,3-dimethoxyphenol (23.64 g; 0.153 mol) was added via syringe. The resulting solution was allowed to warm to room temperature and stirred for two hours. The black solution was cooled to 0° C. and 13.2 ml of chloromethyl methyl ether (14 g; 0.173 mol) was slowly added via syringe. The solution was allowed to reach room temperature and stirred for an additional 8 hours. The yellow mixture was concentrated to an oil that was dissolved in 1000 ml of diethyl ether. The resulting solution was washed with water (500 ml), 2N NaOH (3×400 ml), dried (MgSO$_4$), filtered, and concentrated. After Kugelrohr distillation (90–100° C., 0.3 atm), 24.6 g of a clear oil (84%) was obtained: $^1$H NMR: (300 MHz, CDCl$_3$): 6.97 (t, 1H, J=8.7 Hz); 6.79 (dd, 1H, J=7.2, 1.8 Hz); 6.62 (dd, 1H, J=6.9, 1.2 Hz); 5.21 (s, 2H); 3.87 (s, 3H); 3.85 (s, 3H); 3.51 (s, 3H). CIMS m/z: 199 (M+H$^+$, 50%); 167 (M+H$^+$—CH$_3$OH, 100%). Anal. Calc'd for C$_{10}$H$_{14}$O$_4$: C, 60.59; H, 7.12. Found: C, 60.93; H, 7.16.

2-(3,4-Dimethoxy-2-methoxymethoxyphenyl)-4,4,5,5-tetra-methyl[1,3,2]dioxaborolane (2a).

The MOM-protected phenol 1a (10 g; 0.0505 mol) was dissolved in 1000 ml of dry diethyl ether and cooled to −78° C. A solution of n-butyl lithium (22.2 ml of 2.5 M) was then added via syringe. The cooling bath was removed and the solution was allowed to warm to room temperature. After stirring the solution at room temperature for two hours, a yellow precipitate was observed. The mixture was cooled to −78° C., and 15 ml of 2-isopropoxy-4,4,5,5-tetramethyl-1,3,2-dioxaborolane (0.080 mol) was added via syringe. The cooling bath was removed after two hours. Stirring was continued for four hours at room temperature. The mixture was then poured into 300 ml of water and extracted several times with diethyl ether (3×300 ml), dried (Na$_2$SO$_4$), and concentrated to a yellow oil (12.37 g, 76%) that was used without further purification: $^1$H NMR: (300 MHz, CDCl$_3$): 7.46 (d, 1H, J=8.4 Hz); 6.69 (d, 1H, J=8.4 Hz); 5.15 (s, 2H); 3.87 (s, 3H); 3.83 (s, 3H); 1.327 (s, 12H).

4-Bromo-5-nitroisoquinoline (3a).

Potassium nitrate (5.34 g; 0.052 mol) was added to 20 ml of concentrated sulfuric acid and slowly dissolved by careful heating. The resulting solution was added dropwise to a solution of 4-bromoisoquinoline (10 g; 0.048 mol) dissolved in 40 ml of the same acid at 0° C. After removal of the cooling bath, the solution was stirred for one hour at room temperature. The reaction mixture was then poured onto crushed ice (400 g) and made basic with ammonium hydroxide. The resulting yellow precipitate was collected by filtration and the filtrate was extracted with diethyl ether (3×500 ml), dried (Na$_2$SO$_4$), and concentrated to give a yellow solid that was combined with the initial precipitate. Recrystallization from methanol gave 12.1 g (89%) of slightly yellow crystals: mp 172–174° C.; $^1$H NMR: (300 MHz, CDCl$_3$): 9.27 (s, 1H); 8.87 (s, 1H); 8.21 (dd, 1H, J=6.6, 1.2 Hz); 7.96 (dd, 1H, J=6.6, 1.2 Hz); 7.73 (t, 1H, J=7.5 Hz). CIMS m/z: 253 (M+H$^+$, 100%); 255 (M+H$^+$+2, 100%). Anal. Calc'd for C$_9$H$_5$BrN$_2$O$_2$: C, 42.72; H, 1.99; N, 11.07. Found: C, 42.59; H, 1.76; N, 10.87.

4-(3,4-Dimethoxy-2-methoxymethoxyphenyl)-5-nitroisoquinoline (4a).

Isoquinoline 3a (3.36 g; 0.0143 mol), pinacol boronate ester 2 (5.562 g; 0.0172 mol), and 1.0 g (6 mol %) of tetrakis(triphenylphosphine)palladium(0) were suspended in 100 ml of dimethoxyethane (DME). Potassium hydroxide (3.6 g; 0.064 mol), and 0.46 g (10 mol %) of tetrabutylammonium bromide were dissolved in 14.5 ml of water and added to the DME mixture. The resulting suspension was degassed for 30 minutes with argon and then heated at reflux for four hours. The resulting black solution was allowed to cool to room temperature, poured into 500 ml of water, extracted with diethyl ether (3×500 ml), dried (Na$_2$SO$_4$), and concentrated. The product was then purified by column chromatography (silica gel, 50% ethyl acetate: hexane) giving 5.29 g of yellow crystals (80.1%): mp 138–140° C.; $^1$H NMR: (300 MHz, CDCl$_3$): 9.33 (s, 1H); 8.61 (s, 1H); 8.24 (dd, 1H, J=7.2, 0.9 Hz); 8.0 (dd, 1H, J=6.3, 1.2 Hz); 7.67 (t, 1H, J=7.8 Hz); 7.03 (d, 1H, J=9.6 Hz); 6.81 (d, 1H, J=8.1 Hz); 4.86 (d, 1H, J=6 Hz); 4.70 (d, 1H, J=5.4 Hz); 3.92 (s, 3H); 3.89 (s, 3H); 2.613 (s, 3H). CIMS m/z: 371 (M+H$^+$, 100%). Anal Calc'd for C$_{19}$H$_{18}$N$_2$O$_6$: C, 61.62; H, 4.90; N, 7.56. Found: C, 61.66; H, 4.90; N, 7.56.

2,3-Dimethoxy-6-(5-nitroisoquinolin-4-yl)phenol (5a).

After dissolving isoquinoline 4a (5.285 g, 0.014 mol) in 200 ml of methanol by gentle heating, p-toluenesulfonic acid monohydrate (8.15 g; 0.043 mol) was added in several portions. Stirring was continued for four hours at room temperature. After completion of the reaction, the solution was made basic by adding saturated sodium bicarbonate. The product was then extracted with dichlormethane (3×250 ml), dried (Na$_2$SO$_4$), and concentrated. The resulting yellow solid (4.65 g; 98%) was used directly in the next reaction. An analytical sample was recrystallized from methanol: mp 170–174° C.; $^1$H NMR: (300 MHz, CDCl$_3$): 9.33 (s, 1H); 8.62 (s, 1H); 8.24 (dd, 1H, J=7.2, 0.9 Hz); 7.99 (dd, 1H, J=6.3, 1.2 Hz); 7.67 (t, 1H, J=7.8 Hz); 6.96 (d, 1H, J=8.7 Hz); 6.59 (d, 1H, J=8.7 Hz); 5.88 (bs, 1H); 3.94 (s, 3H); 3.92 (s, 3H). CIMS m/z: 327 (M+H$^+$, 100%). Anal Calc'd for C$_{17}$H$_{14}$N$_2$O$_5$: C, 62.57; H, 4.32; N, 8.58. Found: C, 62.18; H, 4.38; N, 8.35.

8,9-dimethoxychromeno[4,3,2-de]isoquinoline (6a).

Phenol 5a (4.65 g, 0.014 mol) was dissolved in 100 ml of dry N,N-dimethylformamide. The solution was degassed with argon for thirty minutes. Potassium carbonate (5.80 g, 0.042 mol) was added to the yellow solution in one portion. After heating at 80° C. for one hour, the mixture had turned brown and no more starting material remained. After the solution was cooled to room temperature, 200 ml of water was added. The aqueous layer was extracted with dichloromethane (3×500 ml), this organic extract was washed with water (3×500 ml), dried (Na$_2$SO$_4$), and concentrated. A white powder (3.65 g 92%) was obtained that was used in the next reaction without further purification. An analytical sample was recrystallized from ethyl acetate:hexane: mp 195–196° C.; $^1$H NMR: (300 MHz, CDCl$_3$): 9.02 (s, 1H); 8.82 (s, 1H); 7.87 (d, 1H, J=8.7 Hz); 7.62 (m, 3H); 7.32 (dd, 1H, J=6.0, 1.5 Hz); 6.95 (d, J=9.6 Hz); 3.88 (s, 3H); 3.82 (s, 3H). CIMS m/z: 280 (M+H$^+$, 100%).

8,9-dimethoxy-1,2,3,11b-tetrahydrochromeno[4,3,2-de]isoquinoline (7a).

Platinum (IV) oxide (200 mg) was added to a solution containing 50 ml of acetic acid and isoquinoline 6a (1 g; 3.5 mmol). After adding 2.8 ml of concentrated HCl, the mixture was shaken on a Parr hydrogenator at 60 psi for 24 hours. The green solution was filtered through Celite to remove the catalyst and the majority of the acetic acid was removed by rotary evaporation. The remaining acid was neutralized using a saturated sodium bicarbonate solution, extracted with diethyl ether (3×250 ml), dried ($Na_2SO_4$), and concentrated. The resulting oil (0.997 g; 99%) was used without further purification: $^1$H NMR: (300 MHz, $CDCl_3$): 7.10 (t, 1H, J=7.5 Hz); 7.00 (d, 1H, J=8.4 Hz); 6.78 (m, 2H); 6.60 (d, 1H, J=9 Hz); 4.10 (s, 2H); 3.84 (m, 8H); 2.93 (t, 1H, J=12.9 Hz). 8,9-dihydroxy-1,2,3,11b-tetrahydrochromeno[4,3,2-de]isoquinoline hydrobromide (8a).

The crude 7a (0.834 g; 3.0 mmol) was dissolved in 50 ml of anhydrous dichloromethane. The solution was cooled 78° C. and 15.0 ml of a boron tribromide solution (1.0 M in dichloromethane) was slowly added. The solution was stirred overnight, while the reaction slowly warmed to room temperature. The solution was recooled to −78° C., and 50 ml of methanol was slowly added to quench the reaction. The solution was then concentrated to dryness. Methanol was added and the solution was concentrated. This process was repeated three times. The resulting brown solid was treated with activated charcoal and recrystallized from ethanol: mp 298–302° C. dec; $^1$H NMR: (300 MHz, $D_2O$): 7.32 (t, 1H, J=6.6 Hz); 7.13 (d, 1H, J=8.4 Hz); 7.04 (d, 1H, J=8.4 Hz); 4.37 (m, 2H); 4.20 (t, 3H, J=10 Hz). Anal. Calc'd for $C_{15}H_{14}BrNO_3 \cdot H_2O$ : C, 50.87; H, 4.55; N, 3.82. Found: C, 51.18; H, 4.31; N, 3.95.

N-allyl-8,9-dimethoxy-1,2,3,11b-tetrahydrochromeno[4,3,2-de]isoquinoline (10a).

Tetrahydroisoquinoline 7a (1.273 g; 4.5 mmol) was dissolved in 150 ml of acetone. Potassium carbonate (0.613 g; 4.5 mmol) and 0.4 ml (4.6 mmol) of allyl bromide were added. The reaction was stirred at room temperature for four hours. The solid was then removed by filtration and washed on the filter several times with ether. The filtrate was concentrated and purified by flash chromatography (silica gel, 50% ethyl acetate:hexane) to give 1.033 g (71%) of a yellow oil that was used without further purification: $^1$H NMR: (300 MHz, $CDCl_3$): 7.15 (t, 1H, J=9 Hz); 7.04 (d, 1H, J=9 Hz); 6.83 (m, 2H); 6.65 (d, 1H, J=6 Hz); 5.98 (m, 1H); 5.27 (m, 2H); 4.10 (m, 3H); 3.95 (s, 3H); 3.86 (s, 3H); 3.46 (d, 1H, J=15 Hz); 3.30 (d, 2H, J=6 Hz); 2.56 (t, 1H, J=12 Hz).

N-allyl-8,9-dihydroxy-1,2,3,11b-tetrahydrochromeno[4,3,2-de]isoquinoline (11a).

N-Allyl amine 10a (0.625 g; 1.93 mmol) was dissolved in 50 ml of dichloromethane. The solution was cooled to −78° C. and 10.0 ml of $BBr_3$ solution (1.0 M in dichloromethane) was slowly added. The solution was stirred overnight, while the reaction slowly warmed to room temperature. After recooling the solution to −78° C., 50 ml of methanol was slowly added to quench the reaction. The reaction was then concentrated to dryness. Methanol was added and the solution was concentrated. This process was repeated three times. Recrystallization of the brown solid from ethanol gave 0.68 g (61%) of a white solid: mp 251–253° C. dec; $^1$H NMR: (300 MHz, $D_2O$): 10.55 (s, 1H); 10.16 (s, 1H); 8.61 (t, 1H, J=9 Hz); 8.42 (d, 1H, J=9 Hz); 8.31 (d, 1H, J=9 Hz); 7.87 (d, 1H, J=9 Hz); 7.82 (d, 1H, J=9 Hz); 7.36 (q, 1H, J=9 Hz); 6.89 (m, 2H); 6.85 (d, 1H, J=15 Hz); 5.58 (m, 3H); 5.28 (m, 2H); 3.76 (d, 1H, J=3 Hz). HRCIMS m/z: Calc'd: 295.1208. Found: 295.1214.

N-propyl-8,9-dimethoxy-1,2,3,11b-tetrahydrochromeno-(4,3,2-de)-isoquinoline (12a).

N-Allyl amine 10a (1.033 g; 3.2 mmol) was dissolved in 50 ml of ethanol. Palladium on charcoal (10% dry; 0.103 g) was then added. The mixture was shaken on a Parr hydrogenator under 60 psi $H_2$ for 3 hours. After TLC showed no more starting material, the mixture was filtered through Celite and concentrated to give 0.95 g (91%) of an oil that was used without further purification: $^1$H NMR: (300 MHz, $CDCl_3$): 7.15 (t, 1H, J=7.2 Hz); 7.04 (d, 1H, J=8.1 Hz); 6.84 (t, 2H, J=7.5 Hz); 6.65 (d, 1H, J=8.4 Hz); 4.07 (m, 2H); 3.95 (s, 3H); 3.86 (s, 3H); 3.71 (q, 1H, J=5.1 Hz); 3.42 (d, 2H, J=15.6 Hz); 2.62 (m, 2H); 2.471 (t, J=10.5 Hz); 1.69 (h, 2H, J=7.2 Hz); 0.98 (t, 3H, J=7.5 Hz). CIMS m/z: 326 (M+H$^+$, 100%).

N-propyl-8,9-dihydroxy-1,2,3,11b-tetrahydrochromeno[4,3,2-de]isoquinoline (13a).

The N-propyl amine 12a (0.90 g; 2.8 mmol) was dissolved in 200 ml of dichloromethane and cooled to −78° C. In a separate 250 ml round bottom flask, 125 ml of dry dichloromethane was cooled to −78° C., and 1.4 ml (14.8 mmol) of $BBr_3$ was added via syringe. The $BBr_3$ solution was transferred using a cannula to the flask containing the starting material. The solution was stirred overnight, while the reaction slowly warmed to room temperature. After recooling the solution to −78° C., 50 ml of methanol was slowly added to quench the reaction. The reaction was then concentrated to dryness. Methanol was added and the solution was concentrated. This process was repeated three times. The resulting tan solid was suspended in hot isopropyl alcohol. Slowly cooling to room temperature resulted in a fine yellow precipitate. The solid was collected by filtration (0.660 g; 63%): mp 259–264° C. dec; $^1$H NMR: (300 MHz, $CDCl_3$): 7.16 (t, 1H, J=9 Hz); 6.97 (d, 1H, J=12 Hz); 6.83 (d, 1H, J=9 Hz); 6.55 (d, 1H, J=9 Hz); 6.46 (d, 1H, J=9 Hz); 4.45 (d, 1H, J=15 Hz); 4.10 (m, 3H); 3.17 (q, 2H, J=6 Hz); 3.04 (t, 1H, J=9 Hz); 1.73 (q, 2H, J=9 Hz); 0.90 (t, 3H, J=6 Hz). Anal. Calc'd. for $C_{18}H_{20}BrNO_3$: C, 57.16; H, 5.33; N, 3.70. Found: C, 56.78; H, 5.26; N, 3.65.

EXAMPLE 2

Additional Variations of the Subject $D_1$ Agonists

1. Hexahydrobenzo[a]phenanthridines

Additional variations of hexahydrobenzo[a]phenanthridines are set forth with reference to Formula II and are synthesized as described in U.S. Pat. No. 5,420,134 incorporated herein by reference.

2. Dinapsoline

Additional variations of dinapsoline are shown in Table 1 as Compounds 1–47. The compounds in Table 1 are set forth with reference to Formula III and are synthesized as described in U.S. Pat. No. 5,959,110 incorporated herein by reference.

TABLE 1

| Cmpd. Number | R | $R_1$ | $R_2$ | $R_3$ | $R_4$ | $R_5$ | X |
|---|---|---|---|---|---|---|---|
| 1 | H | H | $CH_3$ | H | H | H | OH |
| 2 | H | H | H | $CH_3$ | H | H | OH |
| 3 | H | H | H | H | $CH_3$ | H | OH |
| 4 | H | H | $C_6H_5$ | H | H | H | OH |
| 5 | $CH_3$ | H | $CH_3$ | H | H | H | OH |
| 6 | $C_3H_7$ | H | H | $CH_3$ | H | H | OH |
| 7 | H | H | $C_2H_5$ | H | H | H | OH |
| 8 | H | H | H | $C_2H_5$ | H | H | OH |
| 9 | H | H | H | $CH_3$ | $CH_3$ | H | Br |
| 10 | $C_3H_7$ | H | $CH_3$ | $CH_3$ | H | H | OH |
| 11 | $C_2H_5$ | H | H | $CH_3$ | $CH_3$ | H | Br |
| 12 | $CH_3$ | H | H | H | $C_2H_5$ | H | OH |
| 13 | $C_4H_9$ | H | H | OH | H | H | OH |
| 14 | H | H | $CH_3$ | OH | H | H | OH |
| 15 | H | H | H | F | H | H | OH |
| 16 | H | H | OH | H | H | H | Br |
| 17 | H | H | Br | H | H | H | OH |
| 18 | H | $CH_3$ | H | Br | H | H | $OCH_3$ |
| 19 | H | $CH_3$ | H | H | Br | H | $OCH_3$ |
| 20 | H | $CH_3$ | $CH_3$ | Br | H | H | $OCH_3$ |
| 21 | $CH_3$ | H | F | H | H | H | OH |
| 22 | $CH_3$ | H | H | F | H | H | OH |
| 23 | $CH_3$ | H | H | H | F | H | OH |
| 24 | $C_2H_5$ | H | H | OH | H | H | F |
| 25 | $C_2H_5$ | H | $CH_3$ | OH | H | H | F |
| 26 | $C_2H_5$ | H | $CH_3O$ | H | $CH_3$ | H | F |
| 27 | $C_3H_7$ | H | H | $CH_3O$ | H | H | Cl |
| 28 | $C_3H_7$ | H | H | $CH_3$ | $CH_3O$ | H | Cl |
| 29 | $C_3H_7$ | H | $C_2H_5O$ | H | H | H | OH |
| 30 | $C_3H_7$ | H | H | OH | H | H | OH |
| 31 | $C_4H_9$ | H | $CH_3$ | H | H | H | OH |
| 32 | $C_4H_9$ | H | H | OH | $CH_3$ | H | OH |
| 33 | $C_4H_9$ | H | OH | Cl | H | H | OH |
| 34 | $C_4H_9$ | H | OH | Cl | H | H | OH |
| 35 | $C_4H_9$ | H | H | $CH_3$ | H | H | I |
| 36 | H | H | H | H | H | H | H |
| 37 | H | H | $CH_3$ | H | H | H | H |
| 38 | H | H | H | $CH_3$ | H | H | H |
| 39 | H | H | H | H | $CH_3$ | H | H |
| 40 | H | H | H | H | H | $CH_3$ | OH |
| 41 | H | H | H | H | H | $CH_2(CH_3)_2$ | OH |
| 42 | H | H | H | H | H | $CH_3$ | H |
| 43 | H | H | H | H | H | $CH_2(CH_3)_2$ | H |
| 44 | H | H | $CH_3$ | H | H | $CH_3$ | OH |
| 45 | H | H | H | $CH_3$ | H | $CH_3$ | OH |
| 46 | H | H | H | H | $CH_3$ | $CH_3$ | OH |
| 47 | H | H | H | H | H | $CH_2CH_3$ | OH |

3. Dinoxyline

Using the same general procedures described in Example 1 above, Compounds 1–56 as set forth in Table 2 below are synthesized using starting compounds corresponding to those illustrated in Scheme 1, but substituted with functional groups appropriate to provide the substitution patterns depicted on the fused chromenoisoquinoline product shown for each Example. Thus, for example, 6, 7 and/or 8 substituted analogs of compound 3a (scheme 1) provide the corresponding substituents $R_6$, $R_5$, and $R_4$, respectively on Formula III. Use of other 1 and 3 substituted isoquinolines (analogs of compound 3a in scheme 1) provided corresponding substitution patterns at $C_3$ and $C_1$ in Formula III.

TABLE 2

| Cmpd. Number | $R_1$ | $R_2$ | $R_3$ | $R_4$ | $R_5$ | $R_6$ | $R_8$ | $X_9$ |
|---|---|---|---|---|---|---|---|---|
| 1 | H | H | H | $CH_3$ | H | H | H | OH |
| 2 | H | H | H | H | $CH_3$ | H | H | OH |
| 3 | H | H | H | H | H | $CH_3$ | H | OH |
| 4 | H | H | H | $C_6H_5$ | H | H | H | OH |
| 5 | $CH_3$ | H | $CH_3$ | $CH_3$ | H | H | H | OH |
| 6 | H | H | $C_3H_7$ | H | $CH_3$ | H | H | OH |
| 7 | H | H | H | $C_2H_5$ | H | H | H | OH |
| 8 | H | H | H | H | $C_2H_5$ | H | H | OH |
| 9 | H | H | H | H | $CH_3$ | $CH_3$ | H | Cl |
| 10 | $CH_3$ | H | $C_3H_7$ | $CH_3$ | $CH_3$ | H | H | OH |

TABLE 2-continued

| Cmpd. Number | $R_1$ | $R_2$ | $R_3$ | $R_4$ | $R_5$ | $R_6$ | $R_8$ | $X_9$ |
|---|---|---|---|---|---|---|---|---|
| 11 | $CH_3$ | H | $C_2H_5$ | H | $CH_3$ | $CH_3$ | H | Cl |
| 12 | $CH_3$ | H | $CH_3$ | H | H | $C_2H_5$ | H | OH |
| 13 | $CH_3$ | H | $C_4H_9$ | H | OH | H | H | OH |
| 14 | H | H | H | $CH_3$ | OH | H | H | OH |
| 15 | H | H | H | H | F | H | H | OH |
| 16 | H | H | H | OH | H | H | H | Cl |
| 17 | H | H | H | Br | H | H | H | OH |
| 18 | H | $CH_3$ | H | H | Br | H | H | $OCH_3$ |
| 19 | H | $CH_3$ | H | H | H | Br | H | $OCH_3$ |
| 20 | H | $CH_3$ | H | $CH_3$ | Br | H | H | $OCH_3$ |
| 21 | $CH_3$ | H | $CH_3$ | F | H | H | H | OH |
| 22 | $CH_3$ | H | $CH_3$ | H | F | H | H | OH |
| 23 | $CH_3$ | H | $CH_3$ | H | H | F | H | OH |
| 24 | $C_2H_5$ | H | $C_2H_5$ | H | OH | H | H | F |
| 25 | $C_2H_5$ | H | $C_2H_5$ | $CH_3$ | OH | H | H | F |
| 26 | $C_2H_5$ | H | $C_2H_5$ | $CH_3O$ | H | $CH_3$ | H | F |
| 27 | $C_3H_7$ | H | $C_3H_7$ | H | $CH_3O$ | H | H | Cl |
| 28 | $C_3H_7$ | H | $C_3H_7$ | H | $CH_3$ | $CH_3O$ | H | Cl |
| 29 | $C_3H_7$ | H | $C_3H_7$ | $C_2H_5O$ | H | H | H | OH |
| 30 | $C_3H_7$ | H | $C_3H_7$ | H | H | OH | H | OH |
| 31 | $C_4H_9$ | H | $C_4H_9$ | $CH_3$ | H | H | H | OH |
| 32 | $C_4H_9$ | H | $C_4H_9$ | H | OH | $CH_3$ | H | OH |
| 33 | $C_4H_9$ | H | $C_4H_9$ | OH | Cl | H | H | OH |
| 34 | $C_4H_9$ | H | $C_4H_9$ | OH | Cl | H | H | OH |
| 35 | H | H | H | H | H | H | H | H |
| 36 | H | H | H | $CH_3$ | H | H | H | H |
| 37 | H | H | H | H | $CH_3$ | H | H | H |
| 38 | H | H | H | H | H | $CH_3$ | H | H |
| 39 | H | H | H | H | H | H | $CH_3$ | OH |
| 40 | H | H | H | H | H | H | $CH_2(CH_3)_2$ | OH |
| 41 | H | H | H | H | H | H | $CH_3$ | H |
| 42 | H | H | H | H | H | H | $CH_2(CH_3)_2$ | H |
| 43 | H | H | H | $CH_3$ | H | H | $CH_3$ | OH |
| 44 | H | H | H | H | $CH_3$ | H | $CH_3$ | OH |
| 45 | H | H | H | H | H | $CH_3$ | $CH_3$ | OH |
| 46 | H | H | H | H | H | H | $CH_2CH_3$ | OH |
| 47 | H | $C_3H_5$ | H | H | $CH_3$ | H | H | OH |
| 48 | H | $C_3H_5$ | H | H | H | H | OH | H |
| 49 | H | $C_3H_5$ | H | H | H | H | H | $OCH_3$ |
| 50 | H | $C_3H_5$ | H | H | $C_2H_5$ | H | H | OH |
| 51 | H | $C_3H_5$ | H | $CH_3$ | H | $OCH_3$ | H | OH |
| 52 | H | $C_3H_5$ | H | H | H | H | H | $OCH_3$ |
| 53 | H | $C_3H_5$ | H | H | $CH_3$ | H | H | $OCH_3$ |
| 54 | H | $C_3H_5$ | H | H | H | H | H | OH |
| 55 | H | $C_3H_5$ | H | H | $C_2H_5$ | H | H | OH |
| 56 | H | $C_3H_5$ | H | $OCH_3$ | H | $C_2H_5$ | H | OH |

The foregoing compounds set forth in Tables 1–2 are illustrative of the invention and are not intended to limit the invention to the disclosed compounds. Variations and modifications of the exemplified compounds obvious to one skilled in the art are intended to be within the scope and nature of the invention as specified in the following claims.

EXAMPLE 3

Unilateral 6-OHDA Lesion Model for Parkinson's Disease

Summary. In the rat unilateral 6-hydroxydopamine (6-OHDA) rotation model of Parkinson's disease, 6-OHDA is infused unilaterally into the medial forebrain bundle, the substantia nigra, or the striatum. This treatment results in the destruction of dopamine terminals and neurons and a loss of striatal dopamine, and a profound functional dopaminergic supersensitivity develops on the lesioned side. When challenged with direct-acting dopamine receptor agonists, unilateral 6-OHDA rats turn contralaterally (away from the side of the lesion) because of the increased sensitivity of the postsynaptic dopamine receptors on the lesioned side. The experiments described below examine tolerance induced by the full $D_1$ agonist, dinapsoline, using the 6-OHDA model.

Subjects. Adult male Sprague-Dawley Rats (Hilltop Laboratories, Chatsworth, Calif.), weighing between 280 and 320 grams, were used as subjects. Animals were housed individually with food and water available ad libitum, except as noted below. The light:dark schedule was 12 h:12 h, and testing was performed during the light cycle. All methods adhere to the guidelines in the Guide for the Care and Use of Experimental Animals published by the National Institutes of Health (Pub. 85-23, 1985).

Surgery. Rats were pretreated with 25 mg/kg desipramine (s.c.) approximately 30 minutes before surgery. Rats were anesthetized by inhalation of isoflurane (1.5 to 4.0%) and placed in a stereotaxic apparatus. An infusion cannula was placed in the medial forebrain bundle at the coordinates A.P. −3.8 mm, M.L. −1.5 mm, and D.V. −3.8 mm relative to bregma according to the atlas of Paxinos and Watson (1986). Ten micrograms of 6-OHDA (6-hydroxydopamine; Sigma Chemical Co., St. Louis, Mo.) in a volume of 4 μL was infused at a rate of 0.5 μL/min in a vehicle of 0.01% ascorbate. After a 14-day recovery period, rats were pre-screened for rotation in response to d-amphetamine (5 mg/kg) and to apomorphine (0.3 mg/kg) 1 week later.

Animals that responded to both d-amphetamine (>800 rotations in 3 h) and apomorphine (>100 rotations in 1 h) were retained for further study.

Testing of compounds began on day 28 postsurgery in each case. A new group of 6-OHDA-lesioned rats was used for each new study. In some studies, rats were implanted with a subcutaneous 14-day osmotic minipump (model 2 ML2, Alza, Palo Alto, Calif.) with a flow rate of 5.0 $\mu$L/h. The rats were re-anesthetized with 1.5 to 4% isoflurane, a small incision was made on the back of the neck, and the minipump was placed subcutaneously in the cavity. The incision was closed with sterile wound clips. Before implantation, minipumps were incubated in sterile saline (37° C.) to ensure outflow at the time of implantation. The minipumps were used to administer dinapsoline, or vehicle (50% dimethyl sulfoxide (DMSO), 12.5% ascorbic acid).

Striatal Dopamine Content. In a subset of animals, striatal dopamine content was measured to confirm the extent of the 6-OHDA lesion. At the completion of the study, animals were anesthetized deeply by $CO_2$ inhalation and rapidly decapitated using a guillotine. Brains were removed quickly, and kept on ice while right and left striata were isolated, removed, and weighed in individual nonfilter microcentrifuge tubes containing 0.5 ml of a homogenizing buffer (0.22 N perchloric acid, 0.5% EDTA, 0.15% sodium metabisulfite). The samples were homogenized by sonication for 10 seconds and then centrifuged at 14,000 g for 20 minutes. The supernatant was transferred to microcentrifuge tubes with a filter (0.2 $\mu$m) and centrifuged at 14,000 g for 2 minutes. The samples were frozen at $-80°$ C. to await HPLC analysis.

HPLC Analysis. Thawed samples were analyzed for dopamine content using established high performance liquid chromatography (HPLC)-electrochemical detection methods. Briefly, 50 $\mu$l samples were injected into the sample loop of an HPLC system using an acetate buffer mobile phase (17% methanol) pumped at 0.4 ml/min. Peaks were separated with a C-18 reverse phase column (3-mm diameter, MD-180, ESA, Chelmsford Mass.) and detected with a dual coulometric cell (5014B, ESA) and detector (Coulochem II, ESA). Dopamine was analyzed by sequential reduction (—100 mV) and oxidation (350 mV) and was quantified at the latter electrode. Dopamine concentration in each sample was calculated in reference to established standard curves and was represented as picomoles per milligram of striatal tissue. Depletion was calculated as the percentage of dopamine content on the lesioned side relative to the nonlesioned side.

Apparatus, Procedure, and Statistics. Rats were tested for rotation in automated rotation chambers (Rotoscan, Accuscan, Columbus, Ohio). The apparatus consisted of a cylindrical Plexiglas chamber 30 cm in diameter in which the animal is fitted to a harness attached to a flexible rod connected to a rotating microswitch. Animals were allowed to habituate to chambers for 30 minutes before drug treatment in each case. Data were collected for 1 to 12 h after injection, using 15 minute time bins. Treatments were compared using one-way and repeated measures of analysis of variance (ANOVA), as appropriate; post hoc analysis was performed with Dunnett's test.

Acute Dinapsoline Administration. Beginning 1 week after the screening dose with apomorphine, subjects (n=12) were tested once per week with dinapsoline (0.02, 0.2, or 2 mg/kg) or vehicle (s.c.) using a counterbalanced design, and rotation behavior was monitored for 10 h. After the final day of testing, rats were euthanized and brains were removed for subsequent assessment of dopamine depletion. In the oral dosing experiments, a separate group of subjects (n=8) received dinapsoline (0.02, 0.2, or 2 mg/kg) or vehicle once per week using a counterbalanced design. Rats were fasted for 16 h before dosing with oral gavage, and rotation behavior was monitored for 10 h.

In the experiments that included acute antagonist administration, subjects (n=8/group) were pretreated with either the $D_1$ antagonist SCH-23390 (0.5 mg/kg s.c.; $D_1$ antagonist), the $D_1$ antagonist raclopride (2 mg/kg s.c.), or vehicle. After 30 minutes, they were injected with dinapsoline (0.2 or 2 mg/kg s.c.), and rotation was monitored for 3 h. The shortened assessment period was chosen, because the $D_1$ antagonist SCH-23390 is known to have a relatively short duration of action (approximately 3 h) in our assay.

Chronic Dinapsoline Administration. Subjects (n=5/group) were dosed daily for 14 days at 8 AM every day with either A-77636 (1 mg/kg s.c.) or dinapsoline (2 mg/kg s.c.). In a separate group dinapsoline (2 mg/kg s.c.) or vehicle was administered twice daily at 8 AM and 6 PM everyday. Rotation behavior was monitored in all animals every day for 3 h after the morning injection. In this case, the 3 h assessment period was used to minimize the time that the animals did not have access to food or water.

Coadministration of Dinapsoline with Raclopride. Subjects (n=8/group) were dosed with either raclopride (2 mg/kg s.c.) or vehicle, followed 30 minutes later by dinapsoline (2 mg/kg s.c.) once daily for 6 days. Rotation was monitored for 3 h after dinapsoline administration. On day 7 all animals were challenged with dinapsoline (0.2 mg/kg s.c.) followed by rotation monitoring for 3 h.

Coadministration of A-77636 with Quinpirole. Subjects (n=8/group) were dosed with A-77636 (0.3 mg(kg s.c.) plus either the $D_2$ agonist quinpirole (0.1 mg/kg s.c.), or vehicle for the 2 days. Rotation was monitored for 3 h immediately following quinpirole or vehicle administration. To assess tolerance on day 3, all animals were treated with A-77636 (0.3 mg/kg s.c.) alone followed by rotation monitoring for 3 h. To confirm that the tolerance was specific to $D_1$ receptor desensitization, on day 4, all animals were treated with quinpirole alone (0.1 mg/kg s.c.), and rotation was monitored for 3 h.

Minipump Studies. Rats (n=8/group) were subcutaneously implanted with minipumps calibrated to deliver dinapsoline (0.006, 0.06, 0.6, or 6 mg/kg/day) or vehicle. Behavioral testing for rotation was started at 16 h postimplantation and was monitored for 1 h twice daily. On day 14 after minipump implantation, rats were challenged with dinapsoline (0.2 mg/kg s.c.) and rotation was monitored for 3 h.

Drugs. Dinapsoline was synthesized as described above or as described in Ghosh et al. (1996). SCH-23390, raclopride, A-77636, and quinpirole were obtained from Research Biochemicals International (Natick, Mass.). The vehicle used for dinapsoline was 0.1% ascorbate (Sigma Chemical Co.), and in all other cases sterile water was used as vehicle. In the experiments employing osmotic minipumps, the vehicle was 50% DMSO, and 12.5% EDTA in sterile water.

EXAMPLE 4

Efficacy of Subcutaneously Administered Dinapsoline for Treatment of Parkinson's Disease The procedures were as described in Example 3. The data shown in FIG. 1A represent cumulative rotation (mean±S.E.M.; n=12/group) over 10 hours, and the data shown in FIG. 1B represent mean rotations for each 15 minute time bin during the 10 h test period. When dosed subcutaneously (see FIG. 1A), dinapsoline produced robust, dose-dependent rotational behavior ($F_{3,40}$ 77.3, p<0.001) in the 6-OHDA model. Statistically significant increases in rotation relative to vehicle were obtained at 2.0 and 0.2 mg/kg (p<0.05, Dunnett's test), but not at 0.02 mg/kg. These results demonstrate that dinapsoline administered subcutaneously is efficacious for the treatment of Parkinson's disease based on the 6-OHDA model.

FIG. 1B shows the time course of rotation for each dose. When dosed at 2 mg/kg, dinapsoline produced rotation that lasted approximately 10 h, whereas the effects at 0.2 mg/kg lasted about 5 h. In contrast, the maximal rate of rotation produced by these two doses was comparable, around 150 to 200 rotations per 15 minute time bin. Post-mortem analysis of the dopamine content from the striatum of these animals demonstrated a depletion of 98.1±0.2% (mean±S.E.M.), with a range of 97.3 to 99.8%. A subset of rats was sampled from subsequent experiments, and in all cases depletions were greater than 95%.

EXAMPLE 5

Figure 2:
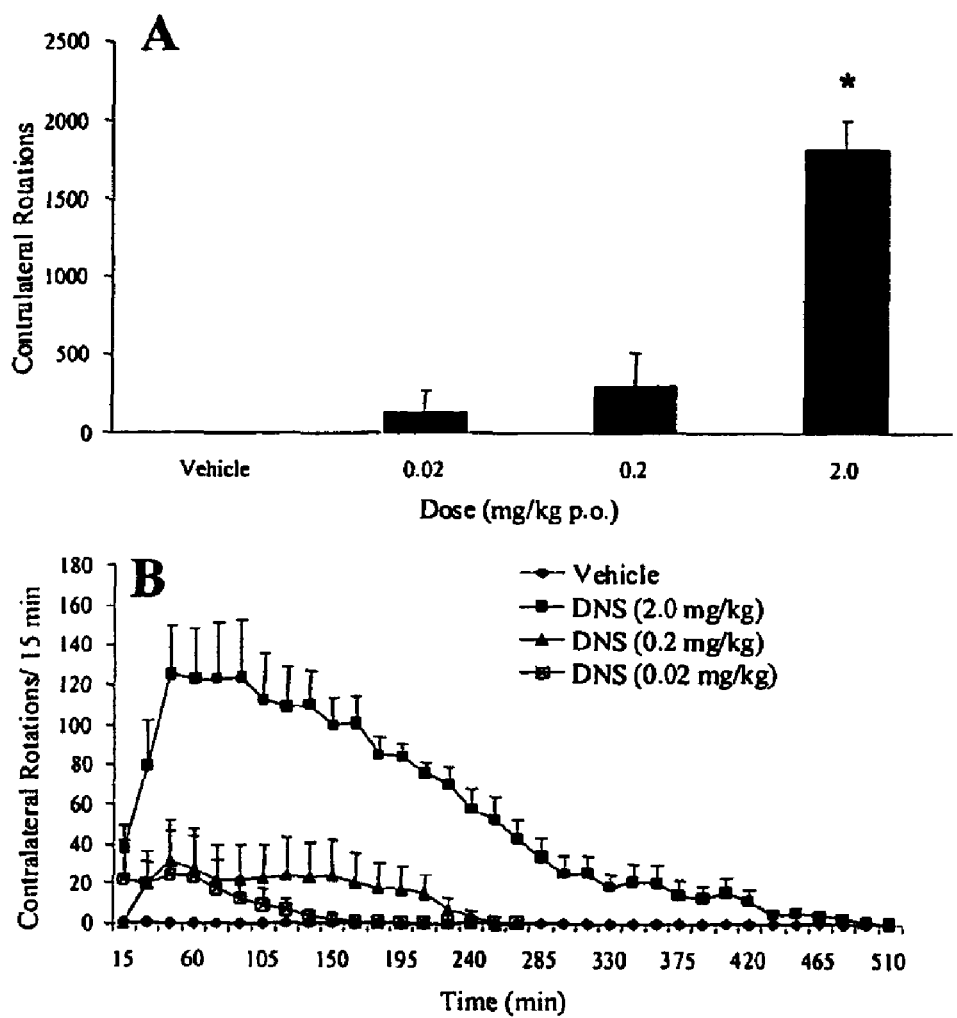
FIG. 2.

Efficacy of Orally Administered Dinapsoline for Treatment of Parkinson's Disease The procedures were as described in Example 3. The data shown in FIG. 2A represent cumulative rotation (mean±S.E.M.; n=8/group) over 10 hours, and the data shown in FIG. 2B represent mean rotations (mean±S.E.M.; n=8/group) for each 15 minute time bin during an 8 h test period. Dinapsoline also produced robust rotation (see FIG. 2A) when administered orally ($F_{3,21}$=42.3, p<0.001), but the response was not dose-dependent. Only the increase in rotation caused by the 2 mg/kg dose was significantly different from baseline (p<0.05, Dunnett's test). As shown in FIG. 2B, when dosed orally at 2 mg/kg, rotation continued to be observed for 7 h. As in Example 4 above, these results demonstrate that orally administered dinapsoline is efficacious for the treatment of Parkinson's disease.

EXAMPLE 6

$D_1$ Receptor Involvement in the Rotational Response to Dinapsoline in the 6-OHDA Model The procedures were as described in Example 3. The data shown in FIGS. 3A and B represent cumulative rotation (mean±S.E.M.; n=8/group) over 3 hours. The rotational response to dinapsoline (see FIG. 3A) was blocked completely by the $D_1$ receptor antagonist SCH-23390 (0.5 mg/kg s.c.). SCH-23390 blocked the rotation produced by dinapsoline administered at 0.2 mg/kg s.c. ($F_{1,14}$=63.8, p<0.001) and 2.0 mg/kg ($F_{1,14}$=95.4, p<0.001). In this experiment rotational behavior was quantified for 3 h to match the known duration of action of SCH-23390.

Figure 3:
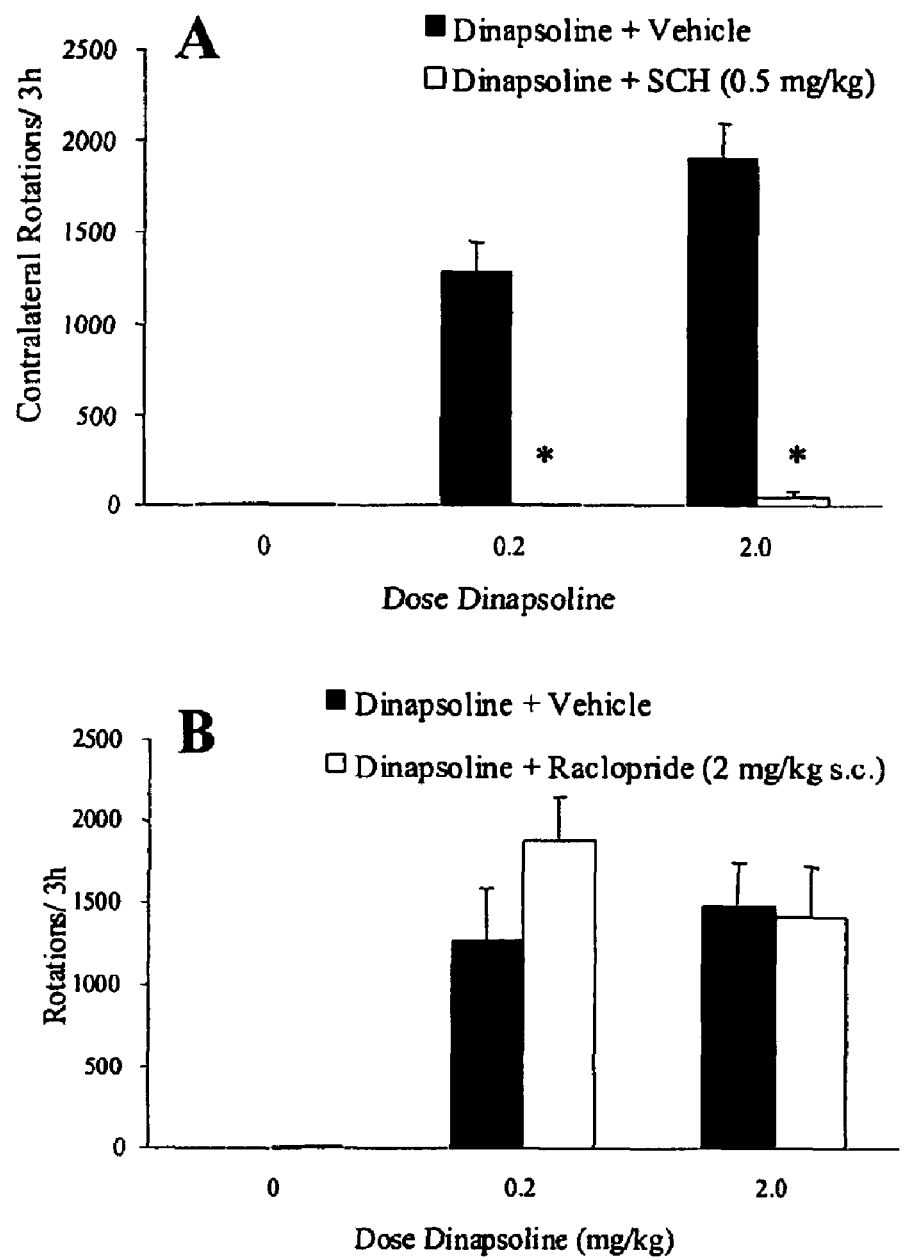
FIG. 3.

As shown in FIG. 3B, the rotational response to dinapsoline was not altered by pre-treatment with the $D_2$ antagonist raclopride (2 mg/kg s.c.). Raclopride (2 mg/kg s.c.) did not reduce the rotational response to dinapsoline at 0.2 mg/kg s.c. ($F_{1,14}$=2.5, p>0.05) or 2 mg/kg s.c. ($F_{1,14}$=0.03, p>0.05). In contrast, the $D_2$ agonist quinpirole (0.25 mg/kg s.c.) produced robust rotation that was blocked completely by raclopride (2 mg/kg s.c.; data not shown). These results demonstrate that the rotational response, indicating the efficacy of dinapsoline for treating Parkinson's disease, can be attributed to activation of $D_1$ dopamine receptors.

EXAMPLE 7

Dinapsoline Dosing Using an Intermittent Daily Regimen and Comparison with A-77636

Figure 4:
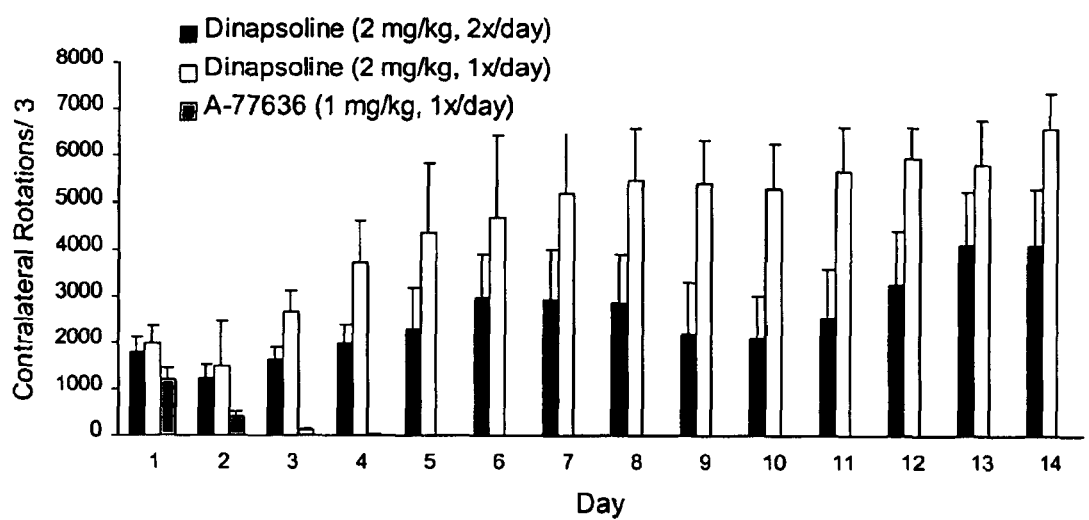
FIG. 4.

The procedures were as described in Example 3. The data shown in FIG. 4 represent cumulative rotation (mean±S.E.M.; n=5/group; 3 hour measuring period) after daily dosing with dinapsoline or A-77636 for 14 days. When A-77636 was dosed once daily at 1 mg/kg s.c. for 14 days, dramatic behavioral tolerance was observed (see FIG. 4). When dosed in naive animals, A-77636 (1 mg/kg s.c.) produced robust rotation, but as early as the second day of dosing, A-77636 produced significantly less rotation than on the first day ($F_{1,13}$=8.5, p=0.012). By the fourth day of dosing, the amount of rotation was no greater than that seen with vehicle ($F_{1,14}$=3.2, p>0.05), indicating that complete tolerance had occurred.

In contrast, no evidence for behavioral tolerance was observed for dinapsoline when dosed once or twice daily at 2 mg/kg s.c. (FIG. 4). As described above, the duration of response to dinapsoline at this dose was about 10 h, whereas A-77636 produced rotation for approximately 18 h when dosed at 1 mg/kg s.c. To account for this difference in duration, a group of animals was dosed twice daily with dinapsoline. Rather than a decrease in response, dinapsoline produced a significant increase in response over time whether dinapsoline was dosed once daily ($F_{13,52}$=42.0, p<0.001) or twice daily ($F_{13,52}$=3.0, p=0.006). These results indicate that dinapsoline produces behavioral sensitization (i.e., the $D_1$ receptors become more sensitive to dinapsoline), rather than tolerance, under intermittent dosing regimens. The once per day dosing regimen produced a stronger sensitizing effect than did the twice per day regimen ($F_{13,104}$=3.1, p=0.009). In contrast, A-77636 has a long plasma half-life (>6 h) and a long duration of action (▲18 h) resulting in persistent $D_1$ receptor stimulation (Asin and Wirtshafter, 1993) that may contribute to the receptor desensitization and the development of tolerance.

EXAMPLE 8

Lack of Involvement of $D_2$ Receptors in Tolerance

Figure 5:
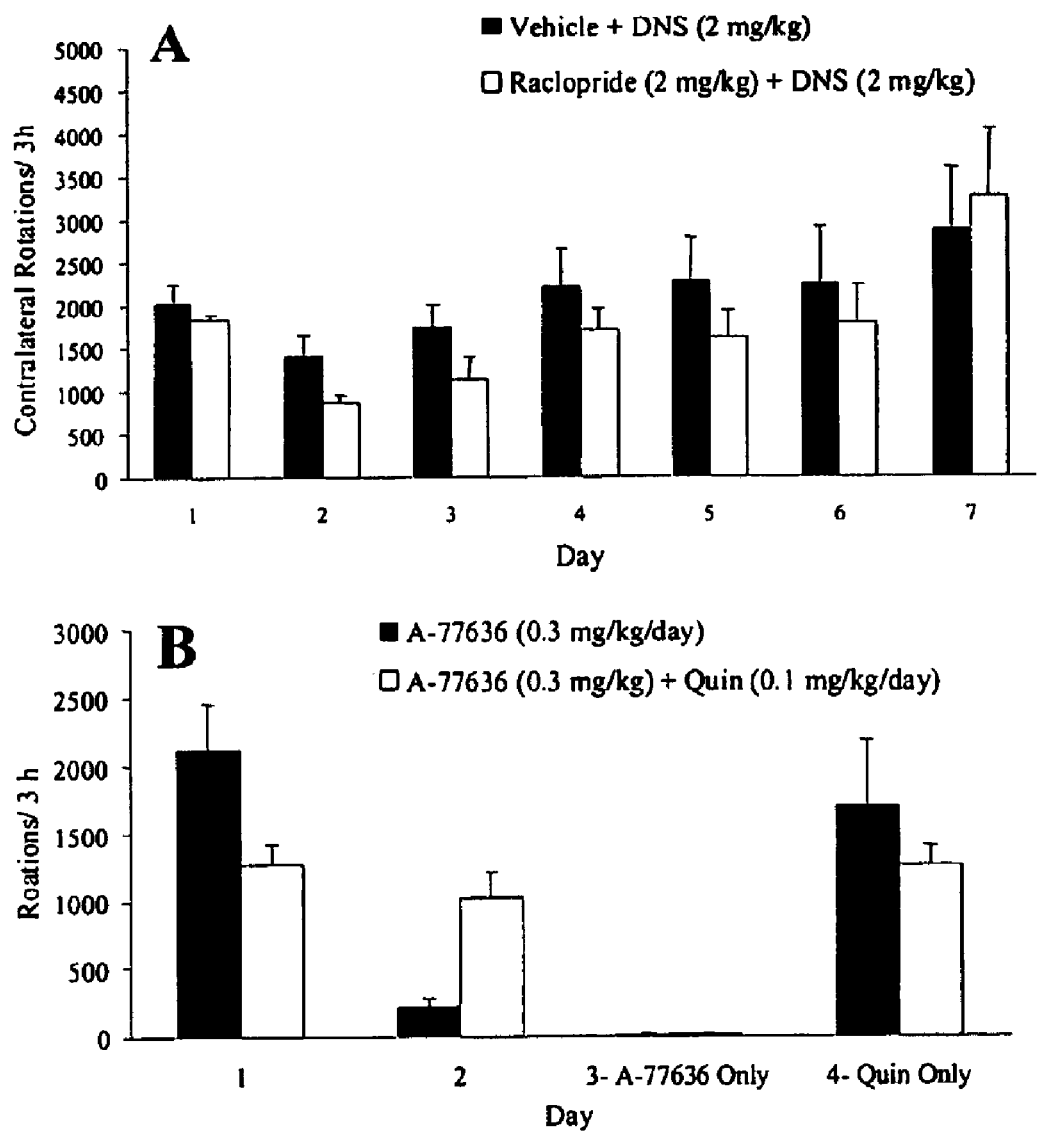
FIG. 5.

The procedures were as described in Example 3. The data shown in FIG. 5A represent cumulative rotation (mean±S.E.M.; n=8/group) over 3 hours after daily dosing with dinapsoline with or without raclopride over 6 days. To assess the basis for the difference in tolerance-producing properties between A-77636 and dinapsoline, the possibility that $D_2$ receptor activity confers some resistance to tolerance was examined (i.e., A-77636 is more strongly $D_1$ selective than dinapsoline). First, the effect of daily coadministration of raclopride (2 mg/kg s.c.) with dinapsoline (2 mg/kg s.c.) for 6 days (FIG. 5A) was determined. There was no significant difference in rotational response to dinapsoline with or without raclopride on days 1 through 6 ($F_{5,45}$=0.2, p>0.05). On day 7, dinapsoline alone was given to both groups (FIG. 5A) to confirm the lack of behavioral tolerance; again no difference was observed ($F_{1,9}$=0.1, p=0.72). These results indicate that $D_2$ agonist activity is not responsible for the lack of tolerance observed with dinapsoline administered in a daily intermittent dosing protocol.

To explore this further, the $D_2$ agonist quinpirole was coadministered subcutaneously in combination with the more selective $D_1$ agonist A-77636. As shown in FIG. 5B, A-77636 alone (black bars) caused a maximal rotational response on day 1, yet significant tolerance by day 2. On day 1, the response in rats treated with both A-77636 and quinpirole (white bars) was somewhat less than that in rats treated with A-77636 alone ($F_{1,13}$=5.9, p=0.03). Conversely, by day 2 ($F_{1,12}$=12.4, p=0.004), the rats treated with A-77636 plus quinpirole had a greater response than those treated with A-77636 plus vehicle (probably due solely to the actions of quinpirole). The challenge dose of A-77636 (0.3 mg/kg s.c.) on day 3 demonstrated equal tolerance in both groups ($F_{1,13}$=0.1, p>0.05), indicating that cotreatment with quinpirole was not "protective." Similarly, on day 4, quinpirole produced equal rotation in both groups, indicating that tolerance was specifically related to $D_1$ receptor function with respect to A-77636. The data shown in FIG. 5B represent cumulative rotation (mean±S.E.M.; n=8/group) over 3 hours produced by a single daily dose of A-77636 with and without quinpirole.

EXAMPLE 9

Continual, Non-Intermittent Administration of Dinapsoline Can Cause Tolerance

Figure 6:
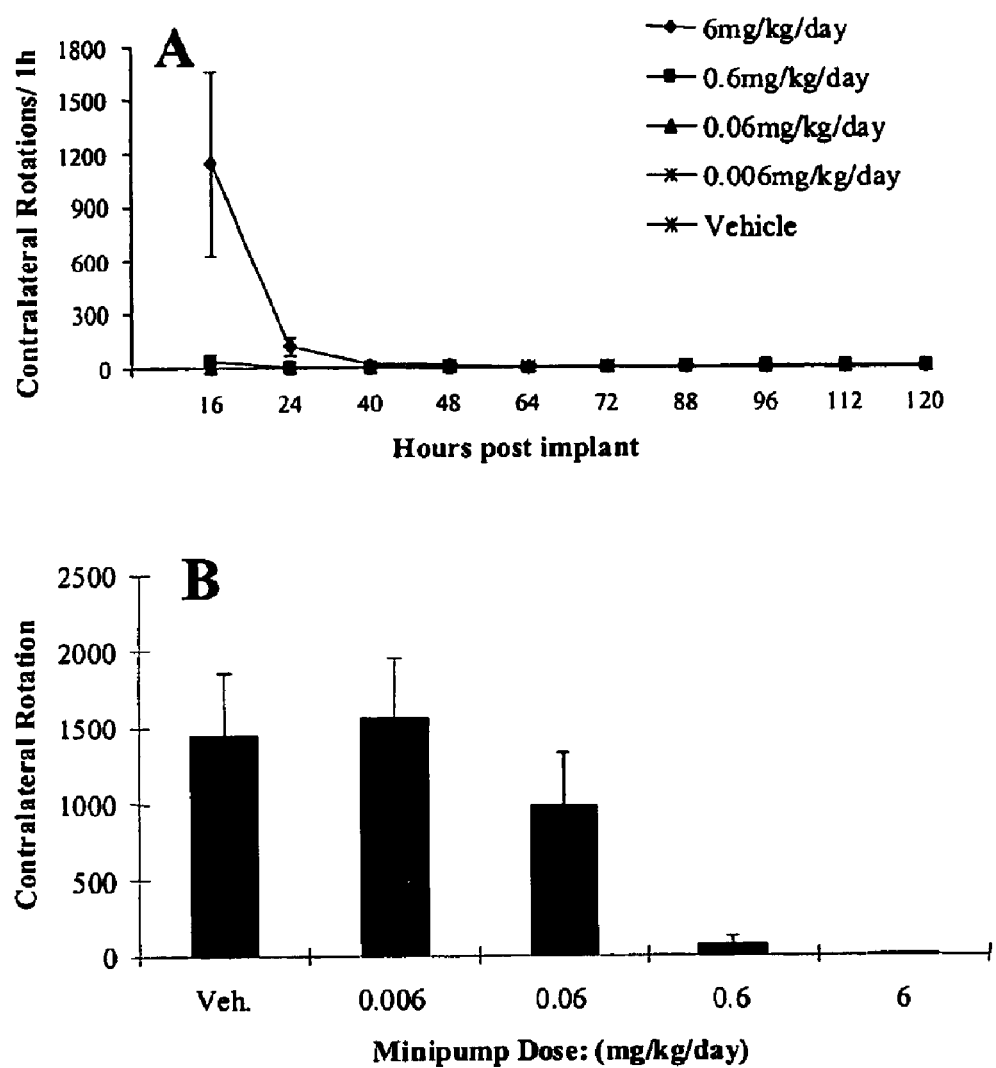
FIG. 6.

The procedures were as described in Example 3. The data shown in FIG. 6A represent cumulative rotation (mean±S.E.M.; n=8/group) per 1 hour time bin at various time points following implantation of osmotic minipumps administering dinapsoline subcutaneously. The data shown in FIG. 6B represent cumulative rotation (mean±S.E.M.) after administration of various doses of dinapsoline by osmotic minipump for 14 days. These experiments tested whether the cause of the difference in response to daily treatment with A-77636 and dinapsoline was related to the pattern of exposure to the drug. Dinapsoline was administered via osmotic minipump, and behavioral testing was performed for 1 h twice daily beginning 16 h after implantation (FIG. 6A). Dinapsoline was administered at four different doses; the highest dose produced a brief behavioral response to which complete tolerance developed by 24 h, whereas the lower doses produced no evidence of rotation. To confirm that the loss of response represents tolerance, a test dose of dinapsoline (0.2 mg/kg s.c.) was given on day 14 after minipump implantation (FIG. 6B). This dinapsoline challenge produced no rotation in the groups that received either 6 or 0.6 mg/kg/day of dinapsoline by minipump, confirming that the loss of effect represented tolerance. These results together indicate that periodic treatment with dinapsoline with an "off-period" prevents development of tolerance whereas continual non-intermittent treatment with dinapsoline results in the induction of tolerance.

What is claimed is:

1. A method for treating a patient with Parkinson's disease resulting from a dopamine-related dysfunction, said method comprising the steps of:

administering to the patient a full $D_1$ agonist selected from the group consisting of dinapsoline, dinoxyline, dihydrexidine, analogs and derivatives of said agonists, and combinations thereof, wherein said agonist has a half-life of less than 6 hours and wherein said agonist is administered periodically at a dose resulting in a first tissue concentration of agonist capable of activating $D_1$ dopainine receptors to produce a therapeutic effect; and reducing said agonist dose at least once every 24 hours to obtain a second lower tissue concentration of agonist wherein said second concentration of agonist results in suboptimal activation of $D_1$ dopamine receptors for a period of time sufficient to prevent induction of tolerance.

2. The method of claim 1 wherein said agonist is administered parenterally.

3. The method of claim 2 wherein said parenteral administration route is selected from the group consisting of intradermal, subcutaneous, intramuscular, intraperitoneal, intrathecal, and intravenous administration.

4. The method of claim 2 wherein said parenteral administration is achieved using a pulsatile release dosage form.

5. The method of claim 2 wherein said parenteral administration is achieved using a metering pump.

6. The method of claim 1 wherein said agonist is administered intranasally.

7. The method of claim 1 wherein said agonist is administered orally.

8. The method of claim 1 wherein said agonist is administered in combination with an antioxidant.

9. The method of claim 1 wherein the period of time for reducing said agonist dose to obtain said second tissue concentration of agonist is at least one hour per each 24-hour dosing period.

10. The method of claim 1 wherein the period of time for reducing said agonist dose to obtain said second tissue concentration of agonist is about one hour to about four hours per each 24-hour dosing period.

11. The method of claim 1 wherein the reducing step includes reducing said agonist dose at least twice every 24 hours to obtain a second lower tissue concentration of agonist.

12. The method of claim 11 wherein the period of time for reducing said agonist dose to obtain said second tissue concentration of agonist is at least one hour per each dosing period.

13. The method of claim 11 wherein the period of time for reducing said agonist dose to obtain said second tissue concentration of agonist is about one hour to about four hours per each dosing period.

* * * * *